(12) United States Patent
Castillo et al.

(10) Patent No.: US 11,946,032 B2
(45) Date of Patent: Apr. 2, 2024

(54) FIXED BED SAMPLER AND RELATED METHODS

(71) Applicant: UNIVERCELLS TECHNOLOGIES S.A., Nivelles (BE)

(72) Inventors: José Castillo, Brussels (BE); Bastien Mairesse, Uccle (BE); Alex Chatel, Brussels (BE); Sebastien Jean-Pierre Michel Rodriguez, Ecaussines-Lalaing (BE); Alexandre VAnhaver, Braine-le-Chateau (BE)

(73) Assignee: UNIVERCELLS TECHNOLOGIES S.A., Nivelles (BE)

( * ) Notice: Subject to any disclaimer, the term of this patent is extended or adjusted under 35 U.S.C. 154(b) by 351 days.

(21) Appl. No.: 16/981,333

(22) PCT Filed: Mar. 18, 2019

(86) PCT No.: PCT/EP2019/056732
§ 371 (c)(1),
(2) Date: Sep. 16, 2020

(87) PCT Pub. No.: WO2019/175442
PCT Pub. Date: Sep. 19, 2019

(65) Prior Publication Data
US 2021/0009933 A1 Jan. 14, 2021

Related U.S. Application Data

(60) Provisional application No. 62/728,405, filed on Sep. 7, 2018, provisional application No. 62/644,014, filed on Mar. 16, 2018.

(30) Foreign Application Priority Data

Mar. 16, 2018 (BE) .................................. 2018/5179

(51) Int. Cl.
*C12M 1/12* (2006.01)
*C12M 1/26* (2006.01)
*C12M 3/00* (2006.01)

(52) U.S. Cl.
CPC ............ *C12M 25/18* (2013.01); *C12M 23/46* (2013.01); *C12M 33/18* (2013.01)

(58) Field of Classification Search
CPC ...... C12M 25/18; C12M 23/46; C12M 33/18; C12M 25/02; C12M 33/02; C12M 47/16
See application file for complete search history.

(56) References Cited

U.S. PATENT DOCUMENTS 4,734,373 A   3/1988  Bartal
5,266,476 A * 11/1993 Sussman .............. C12N 5/0068
                                                        435/399

(Continued)

FOREIGN PATENT DOCUMENTS

CN        102994377 A       3/2013
JP        2001120255 A      5/2001

(Continued)

OTHER PUBLICATIONS

Yang et. al. "A Fibrous-Bed Bioreactor for Continuous Production of Monoclonal Antibody by Hybridoma" Adv Biochem Engin/Biotechnol (2004) 87: 61-96 (Year: 2004).*

(Continued)

*Primary Examiner* — William H. Beisner
*Assistant Examiner* — Danielle B Henkel
(74) *Attorney, Agent, or Firm* — Dickinson Wright PLLC; Andrew D. Dorisio

(57) ABSTRACT

A sampler for use with a bioreactor for growing a cell culture is disclosed. In one embodiment, the bioreactor includes a structured fixed bed including a removable sample portion (Continued)

for recovering a sample of cells from the cell culture. Related apparatuses and methods are also disclosed.

11 Claims, 32 Drawing Sheets

(56) References Cited

U.S. PATENT DOCUMENTS

| | | |
|---|---|---|
| 2010/0099127 A1 | 4/2010 | Bodner |
| 2013/0071872 A1 | 3/2013 | Ho et al. |
| 2014/0030805 A1* | 1/2014 | Kasuto .................. C12N 5/0605 |
| | | 435/366 |
| 2014/0193901 A1 | 7/2014 | Lee et al. |
| 2016/0281045 A1* | 9/2016 | McCall .................. C12M 23/40 |
| 2017/0022465 A1* | 1/2017 | Ho .......................... C12M 27/20 |
| 2019/0031998 A1* | 1/2019 | Valonen .................. C12M 29/10 |
| 2020/0165557 A1* | 5/2020 | Lesch .................... C12M 25/18 |

FOREIGN PATENT DOCUMENTS

| | | |
|---|---|---|
| JP | 2007500505 A | 1/2007 |
| KR | 20060054362 A | 5/2006 |
| WO | WO2022216568 A1 | 10/2022 |

OTHER PUBLICATIONS

Lewis et. al. Continuous Propionic Acid Fermentation by Immobilized Propionibacterium acidipropionici in a Novel Packed-Bed Bioreactor Biotechnology and Bioengineering, vol. 40, pp. 465-4T4 (1992) (Year: 1992).*

Valkama, Optimization of lentiviral vector production for scale-up in fixed-bed bioreactor (Year: 2017).*

Anzola-Rojas Melida Del Pilar et al.; "Improvement of hydrogen production via ethanol-type fermentation in an anaerobic down-flow structured bed reactor"; Bioresource Technology, Netherlands, 2015.

* cited by examiner

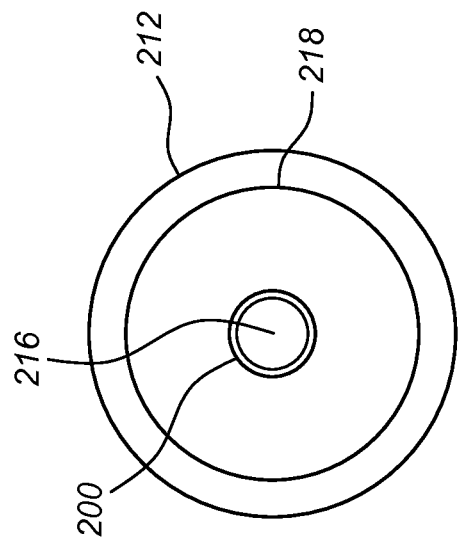
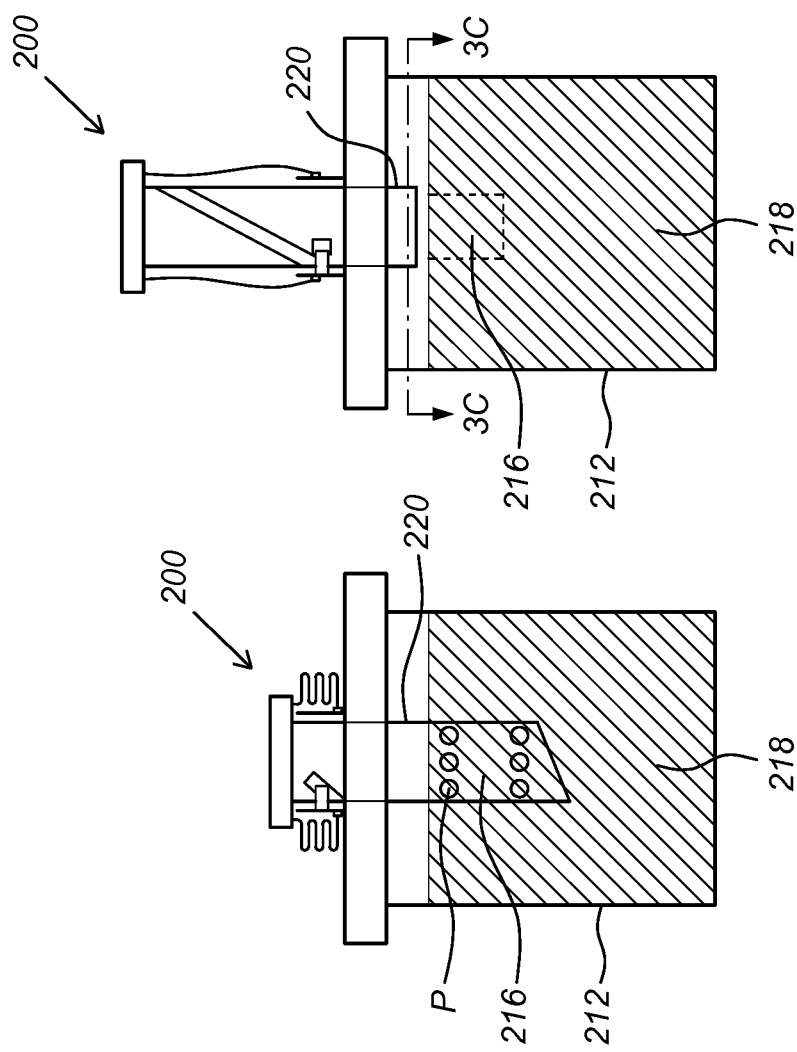
Fig. 3C
Fig. 3B
Fig. 3A

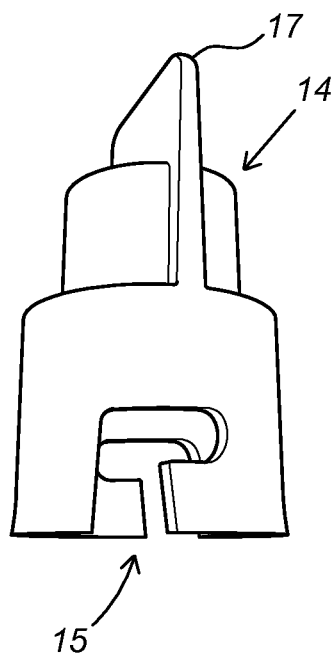
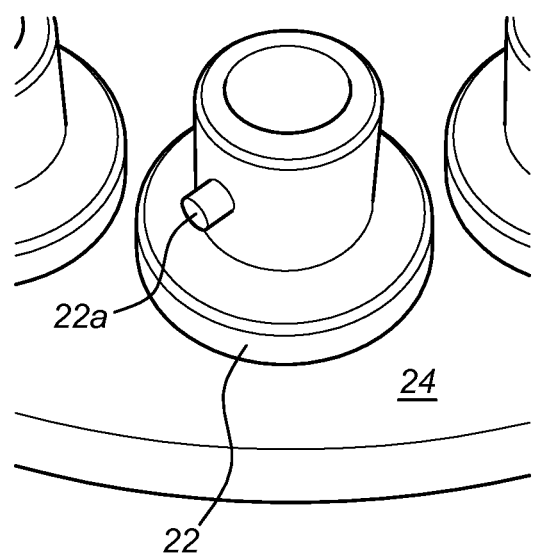
Fig. 4     Fig. 5
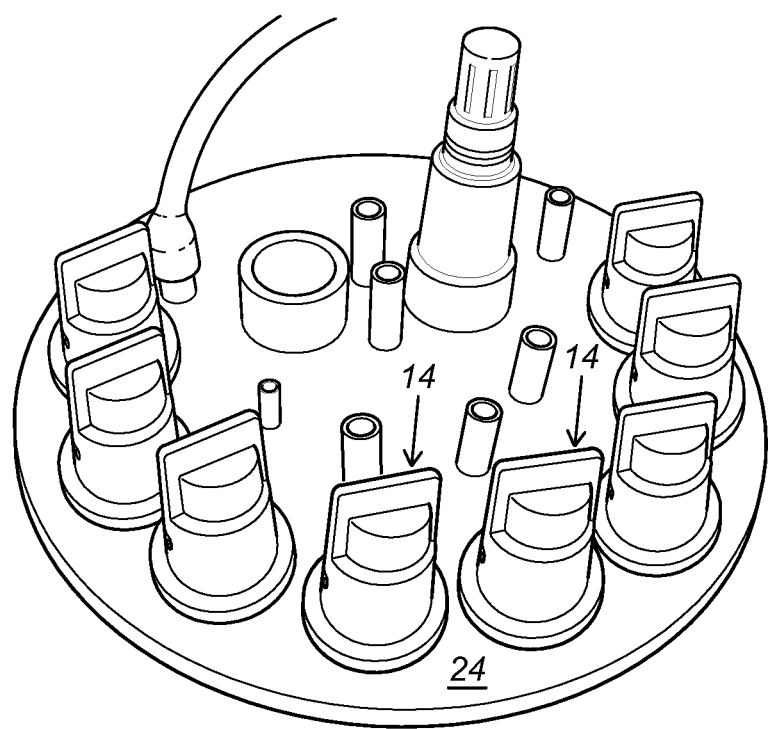
Fig. 6

FIXED BED SAMPLER AND RELATED METHODS

This patent application claims the benefit of U.S. Provisional Patent Application Ser. Nos. 62/728,405, 62/644,014, and Belgian Patent Application BE2018/5179, the disclosures of which are incorporated herein by reference. The disclosures of U.S. Patent Application Publication No. 2018/0282678, International Patent Application PCT/EP2018/076354, U.S. Provisional Patent Application 62/711,070, and U.S. Provisional Patent Application 62/725,545 are incorporated herein by reference.

TECHNICAL FIELD

This document relates generally to the cell culturing arts and, more particularly, to a sampler for a fixed bed cell culturing device and related methods.

BACKGROUND

Certain cell culturing devices, such as bioreactors, use a "fixed bed" for the growth of cells that are entrapped thereon or for the growth of adherent cells which attach and grow thereon. These high cell density bioreactors suffer from the inherent inability of its users to easily take samples at any point before, during or after the culture process for various purposes (e.g., to take cell-associated measurements such as those relating to viability and density). Currently, the only way to take such an in-process sample from the fixed bed is to reach inside the bioreactor with a tool such as a tweezer during operation, and to manually extract a piece or portion of the bed. This operation is difficult as it requires careful dexterity. Also, it invariably causes undesirable perturbations that risk disrupting the cell culture environment, as well as the sample specimen.

Furthermore, to maintain the necessary sterile conditions, the bioreactor is typically located inside a containment unit such as a laminar flow cabinet or a biosafety cabinet where the freedom of movement and access of the operator for such a maneuver is limited. While a small scale bioreactor can be placed in such a containment unit, a large production-scale version cannot readily be placed in such cabinets to achieve this result. Additionally, sterility must be maintained during the whole operation, which means the operator collecting the sample has to follow precise aseptic operating procedures. This is challenging when having to introduce an extraction tool such as a tweezer.

Sterile (or aseptic) sensors, such as so-called "biomass" sensors have been proposed for assessing cell density. However, these sensors lack sufficiently robust technology, and do not allow for the actual direct examination of the cells as a sample. Indirect measurement of cell characteristics by the biomass sensor is far less accurate than direct examination of cells. Also, as opposed to the case of fluidized beds or classical agitated bioreactors where sampling of the liquid in which the cells reside is possible, a sterile liquid sensor in a fixed bed bioreactor yields only information from which an educated guess or estimate can be made regarding cell conditions based on detected byproducts (metabolites) of the growth process left in the fluid. Thus, current samplers and methods do not provide an accurate and timely tool for developing a reliable cell culture process for a fixed bed bioreactor.

Accordingly, a need is identified for a device that provides the ability to take a reliable sample from the fixed bed and the cells associated therewith. The device would allow for the sample to be obtained in an easy and inexpensive manner, while maintaining aseptic conditions so as to protect against contamination (both internal to the bioreactor and external to it) and to avoid creating deleterious disruptions of the fixed bed cell culture environment.

SUMMARY

An object of the invention is to provide a device that enables the taking of one or more samples from the cell culture in an easy, inexpensive, and reliable manner, while maintaining aseptic or sterile conditions, and also while avoiding creating deleterious disruptions of the fixed bed cell culture environment.

According to one aspect of the disclosure, a sampler is provided for a fixed bed in which cells are grown, such as a cell culturing device or bioreactor. The sampler is proposed in several formats: (1) one which allows the operator to take a sample in a non-sterile manner (such as when the bioreactor is present in a laminar flow cabinet or a biosafety cabinet); (2) one which allows the operator to take a sample in a sterile manner; and (3) another which allows a larger volume or portion of the fixed bed to be extracted, an operation desirable at an or the end of a cell culture process. For the latter versions, the sterility of the sampling process itself ensures that the bioreactor is not constrained to being operated in a sterile environment, while ensuring protection both for the process and the environment. The sampler thereby improves the operability of the bioreactor by facilitating: (a) the operation required to take a sample from the fixed bed cell culture (manually, or possibly via partial or full automation) without deleterious disruption or effects, and (b) the containment and sterility constraints associated with fixed bed bioreactors, in such a way that it can be operated outside of a strictly sterile zone without risking contamination of the bioreactor itself or the sample by the environment, and the environment by the content of the bioreactor or the sample. However, a proposal is also made for a sampler that can be used in a situation where the cell culturing device (bioreactor) is operated in a sterile environment as well (e.g., a small size (e.g., <600 m2 surface area) bioreactor that can be used in connection with an isolator, cabinet, or the like).

According to one aspect of the disclosure, an apparatus for use with a cell culture system, such as for example a bioreactor, fermenter, or the like, is disclosed. The apparatus comprises a structured fixed bed including a removable sample portion for recovering a sample of cells from the cell culture system.

In some embodiments, the structured fixed bed comprises at least two layers of material adjacent to each other, the removable sample portion being located at least partially between the at least two layers. In some embodiments, the at least two layers comprise: (1) cell immobilization layers, and the removable sample portion has a first side in contact with a first cell immobilization layer and a second side in contact with a second cell immobilization layer; or (2) one cell immobilization layer and one spacer layer. In some embodiments, the removable sample portion comprises one or more fibers, and in some embodiments, removable sample portion comprise a non-woven material. In any embodiment, the removable sample portion may comprise a sheet of material. In some embodiments, the structured fixed bed comprises a cell immobilization layer, and the sheet of material forming the removable sample portion is in direct contact with the cell immobilization layer.

In some embodiments, the apparatus comprises a positioner mechanically connected to the removable sample portion by a connector. In some embodiments, the structured fixed bed comprises a plurality of removable sample portions. In some embodiments, the structured fixed bed comprises a roller or spiral bed, and in some embodiments the removable sample portion is adjacent to the structured fixed bed, and in some embodiments the removable sample portion is a perforated or pre-cut portion of the structured fixed bed.

The apparatus of any disclosed embodiment may be applied to a bioreactor. In one exemplary form, the bioreactor comprises an outer chamber for receiving the structured fixed bed with an upward flow of fluid. An inner chamber is provided for returning fluid flow to a lower portion of the bioreactor including an agitator.

According to another aspect of the disclosure, an apparatus for use with a bioreactor for growing a cell culture is provided. The apparatus comprises a fixed bed including a removable sample portion comprising one or more fibers for recovering a sample of cells from the cell culture.

In some embodiments, the fixed bed comprises an unstructured fixed bed. In some embodiments, the fixed bed comprises a structured fixed bed. In some embodiments, the removable sample portion comprises a non-woven material. In some embodiments, the removable sample portion is between two layers of the fixed bed, and in some embodiments, the removable sample portion is adjacent to the fixed bed (or both approaches are combined). In these or other embodiments, the removable sample portion is a perforated or pre-cut portion of the structured fixed bed.

In some embodiments, the sample portion may be in contact with the fixed bed in a bioreactor and need not be inserted or positioned within it. In some embodiments the sample portion may be positioned adjacent to and in contact with a surface of the fixed bed, such as a side surface or an upper surface thereof, and connected to the positioner. In some embodiments the sample portion comprises a folded portion. In some embodiments, the sample portion comprises a folded portion and a welded portion.

According to yet another aspect of the disclosure, an apparatus for sampling a cell culture is provided. The apparatus comprises a bioreactor comprising a structured fixed bed including a removable sample portion. A sampler is associated with the bioreactor for recovering the removable sample portion from the structured fixed bed.

In some embodiments, the removable sample portion includes a positioner adapted for positioning the sample portion within the structured fixed bed, the positioner being accessible via a port in the bioreactor. In some embodiments, a support is associated with the port by way of a releasable connection, such as a bayonet fitting including a slot on the support and a post on the port, a threaded connection, or a releasable latch, the support being connected to the positioner. In some embodiments, the support is fixed to the positioner, or releasably connected to the positioner, such as by a flexible portion for releasably engaging a portion of the positioner for movement together in an axial direction, but allowing for the support to rotate without imparting rotation to the positioner. In some embodiments, the support comprises a frangible connection for separating the support into multiple portions for removal of the removable sample portion.

In some embodiments, the sampler comprises a cutter for forming the removable sample portion of the structured fixed bed. In some embodiments, the sampler comprises a groove for engaging a locking pin associated with the port for guiding the sampler into position.

In some embodiments, a container is provided for maintaining a sterile condition of the removable sample portion when removed from the bioreactor. In some embodiments, the container connects to the bioreactor via an aseptic connection so as to maintain a sterile condition within a compartment defined by the container and including the sampler, and also a sterile condition of the bioreactor. In some embodiments, the container comprises a septum for receiving a connector connected to the removable sample portion. In some embodiments, the container comprises a flexible sleeve, which in some embodiments is connected to a rigid elbow.

In some embodiments, the removable sample portion includes a positioner connected to the removable sample portion, the positioner being associated with an actuator for withdrawing the removable sample portion from the structured fixed bed. In some embodiments, the actuator comprises a stator and a rotor. In some embodiments, the actuator is connected to a sleeve for receiving a positioner connected to the sample portion. In some embodiments, the stator comprises a flexible bag surrounding the rotor. In some embodiments, the stator comprises a cradle for cradling the rotor.

In some embodiments, a controller is provided for controlling the actuator. In some embodiments, the controller is adapted for receiving an output signal from at least one sensor associated with the bioreactor.

In some embodiments, the removable sample portion is connected to a positioner forming a releasable connection with a cap for a port of the bioreactor. In some embodiments, the releasable connection comprises a magnetic coupling. In some embodiments, the port includes a receiver for receiving a projection of the positioner in a manner that prevents relative rotate In any disclosed embodiment, the structured fixed bed may comprises a roller or spiral bed. In some embodiments, the removable sample portion is adjacent to the structured fixed bed. In some embodiments, the removable sample portion is a perforated or pre-cut portion of the structured fixed bed.

Still further, the disclosure pertains to an apparatus for sampling a cell culture. The apparatus comprises a bioreactor comprising a bed including a removable sample portion and a sampler associated with the bioreactor for recovering the removable sample portion from the bed. The sampler comprises a positioner releasably connected to the removable sample portion.

In some embodiments, the positioner is releasably connected to the removable sample portion by a clamp. In some embodiments, the removable sample portion is within or adjacent to the structured fixed bed. In some embodiments, the removable sample portion is a perforated or pre-cut portion of the structured fixed bed.

Yet another aspect of the disclosure pertains to an apparatus for sampling a cell culture associated with a bed in a bioreactor having a port. The apparatus comprises a sampler associated with the bioreactor for recovering a sample portion of the bed via the port, the sampler including an actuator for withdrawing the sample portion from the bed.

In some embodiments, the actuator is connected to a container for receiving a positioner connected to the sample portion. In some embodiments, the actuator comprises a stator and a rotor. In some embodiments, the stator comprises a flexible bag surrounding the rotor.

In some embodiments, the stator comprises a cradle for cradling the rotor. In some embodiments, a controller is provided for controlling the actuator. In some embodiments, the controller is adapted for receiving an output signal from at least one sensor associated with the bioreactor.

In some embodiments, the bed comprises a structured fixed bed including at least two layers, and the sample portion comprises a sheet of material located between at least two layers. In some embodiments, the removable sample portion is within or adjacent to the structured fixed bed. In some embodiments, the removable sample portion is a perforated or pre-cut portion of the structured fixed bed.

A further aspect of this disclosure pertains to a method of sampling a cell culture in cell culture system, such as a bioreactor having a structured fixed bed. The method includes the step of recovering a removable sample portion from the structured fixed bed of the bioreactor. In some embodiments, the structured fixed bed comprises at least two layers, and the method comprises positioning the removable sample portion at least partially between the at least two layers prior to the recovering step.

In some embodiments, the recovering step comprises withdrawing a positioner connected to the removable sample portion from the bioreactor until the removable sample portion is received in a container connected to the bioreactor by an aseptic connector. In some embodiments, the withdrawing step comprises using an actuator controlled by a controller based on a sensed condition of the bioreactor. In some embodiments, any or all of the following steps are performed: (1) counting the cells removed on the removable sample portion; (2) coloration of the cells or (3) extracting intra-cell viruses from the cells removed on the removable sample portion.

Still further, the disclosure pertains to a method for inserting a sample portion in a fixed bed having two or more layers, comprising positioning the sample portion within or adjacent to the two or more layers of the fixed bed.

Yet another aspect of the disclosure is a method for manufacturing a fixed bed wherein the fixed bed comprises one or more sample portions, the method comprising introducing means for detaching the sample portion from the rest of the fixed bed.

In some embodiments, the method includes the step of perforating or pre-cutting the bed to form the one or more sample portions. In some embodiments, the method includes the step of growing cells on the one or more sample portions.

BRIEF DESCRIPTION OF THE DRAWING FIGURES

The novel features of the disclosure are set forth with particularity in the appended claims. A better understanding of the features and advantages of the present disclosure will be obtained by reference to the following detailed description that sets forth illustrative embodiments, in which the principles of the invention are utilized, and the accompanying drawings of which:

Figure 1:
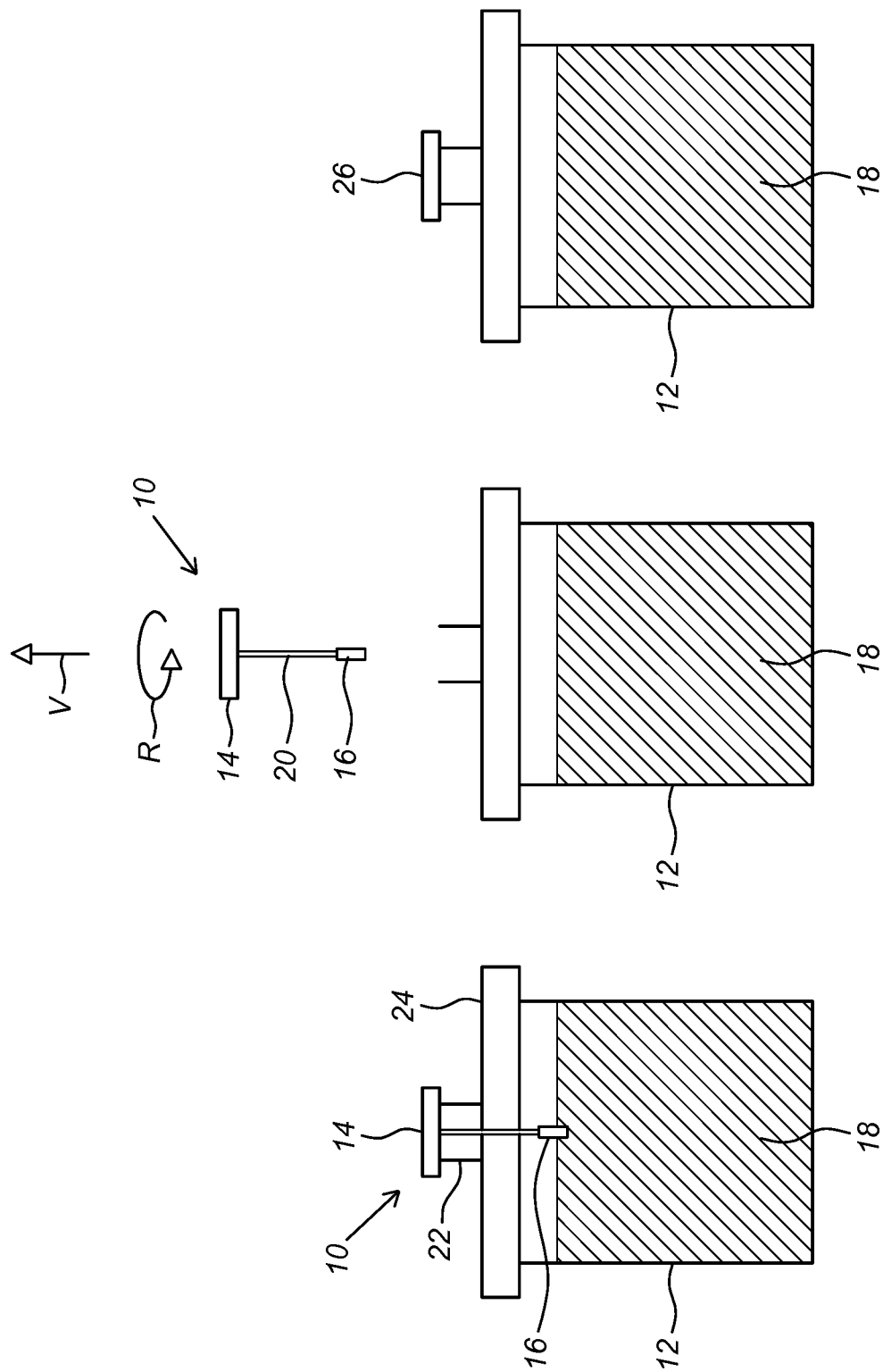
FIG. 1 is a schematic view of a first embodiment of a sampler for a cell culture system, such as a bioreactor, according to the disclosure.
Figure 1A:
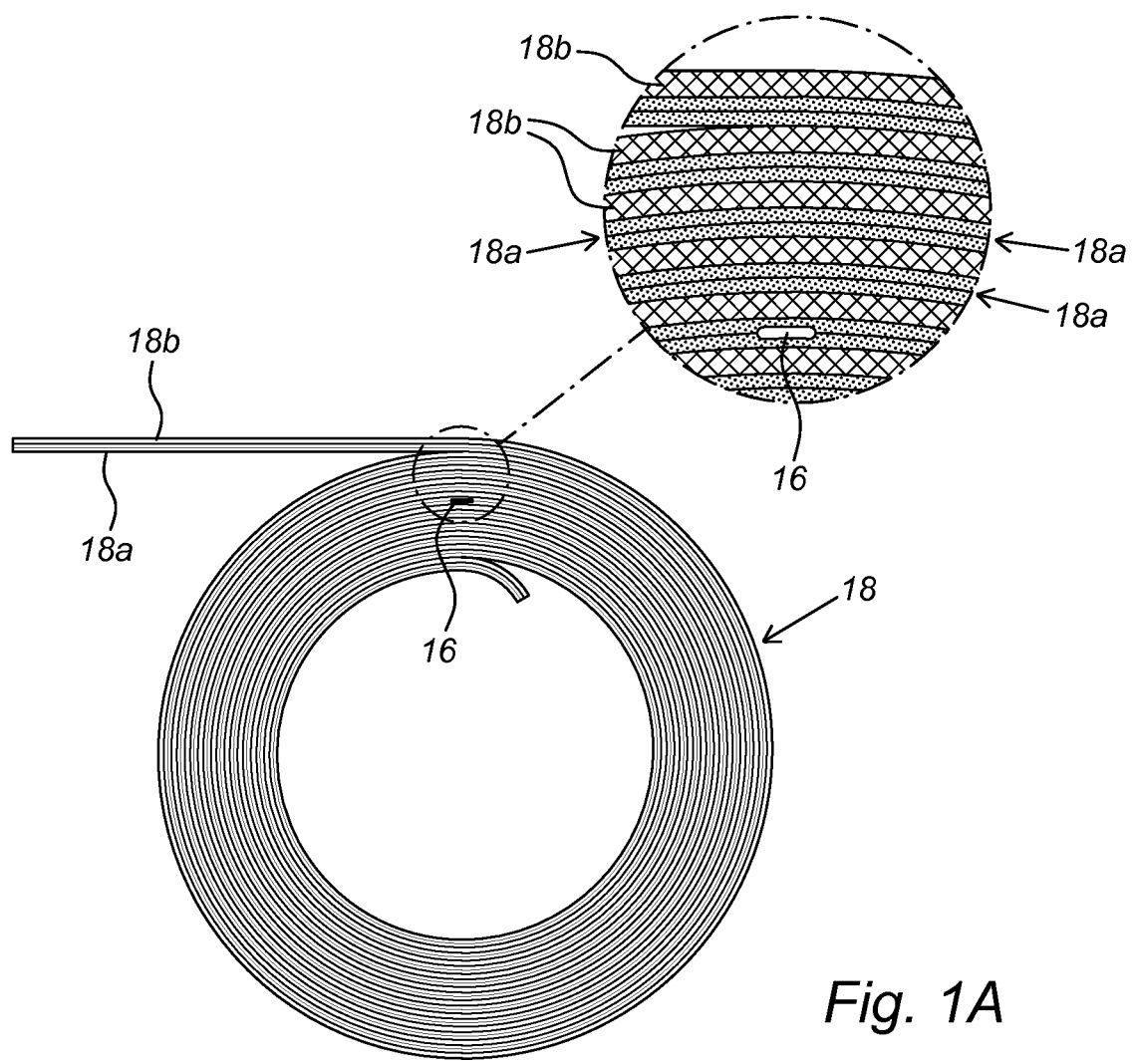
FIG. 1A illustrates one example of a structured fixed bed in the form of a spiral bed.
Figure 1B:
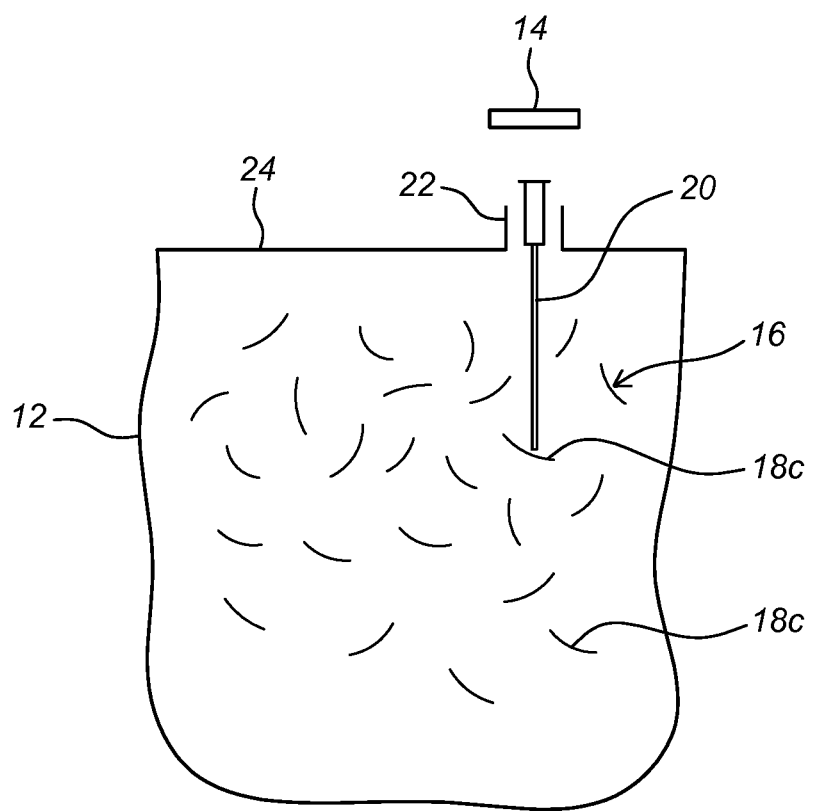
FIG. 1B is a schematic view illustrating a sampler in use in an unstructured fixed bed, where a positioner includes at least one fiber.
Figure 1C:
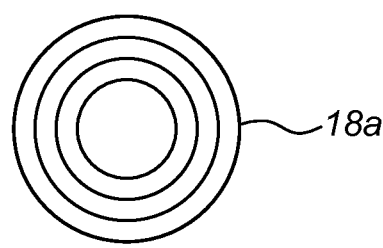
FIG. 1C illustrates alternate forms of a structured fixed bed.
Figure 1C:
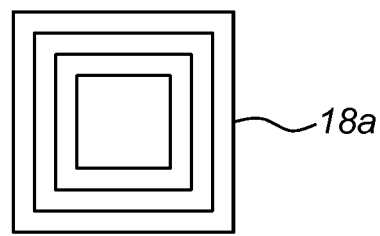
Figure 1C:
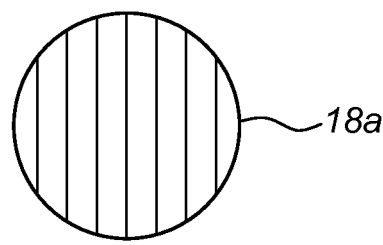
Figure 1D:
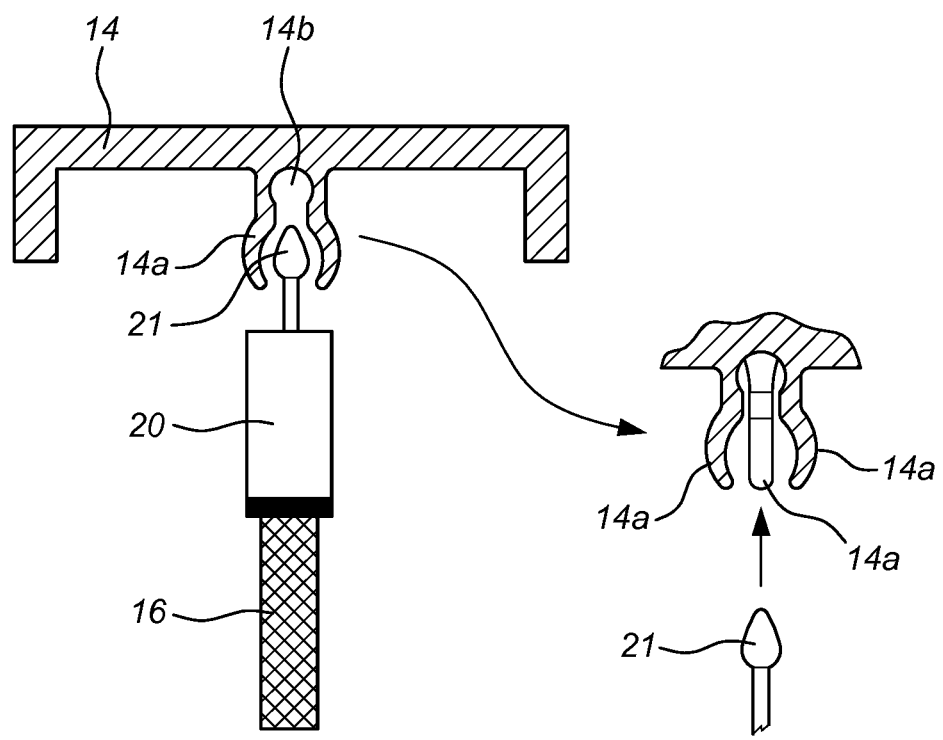
Figure 1E:
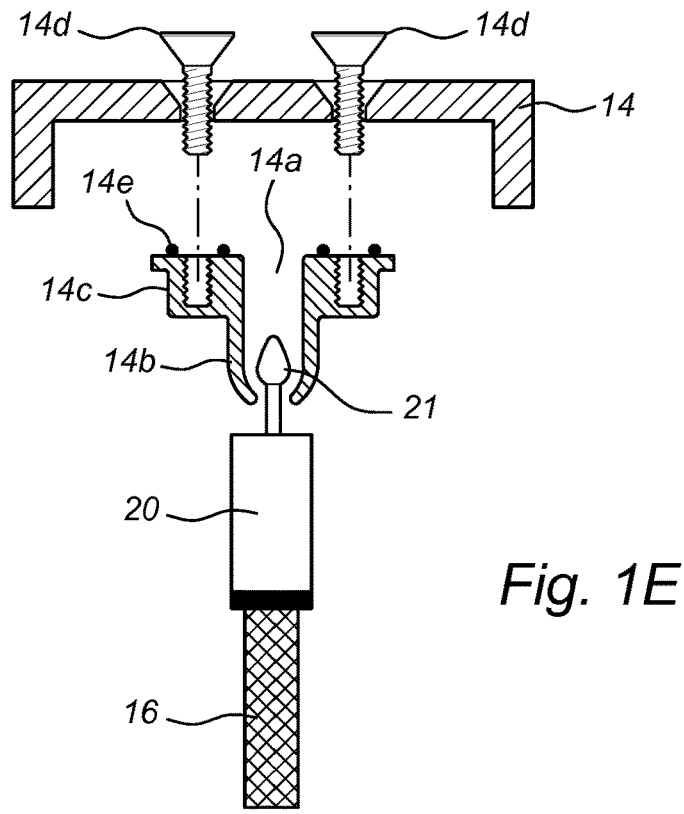
Figure 1F:
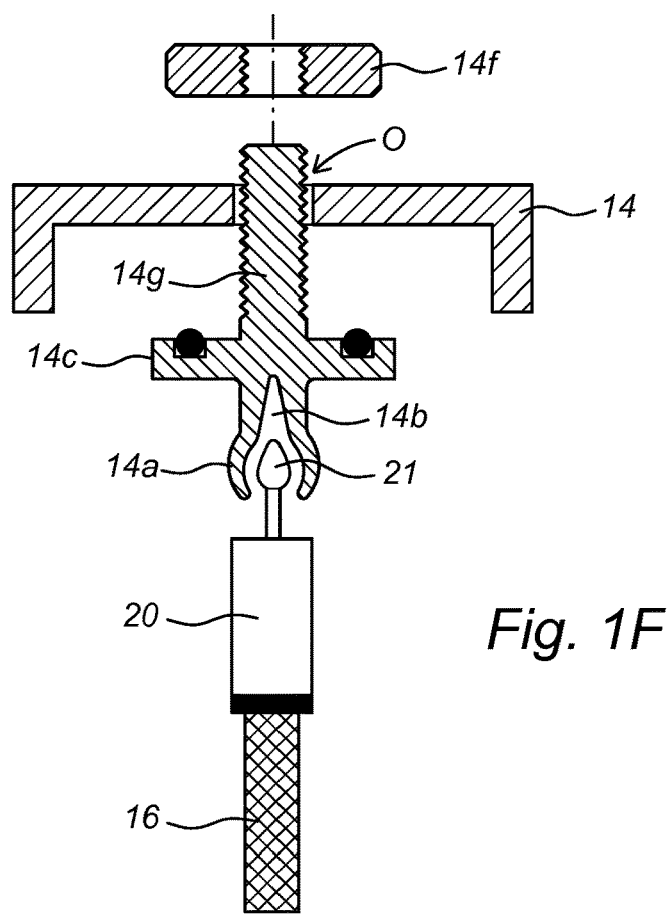

FIGS. 1D, 1E, and 1F illustrate various manners of or steps for locating a positioner connected to a removable sample portion to a bioreactor.

Figure 2:
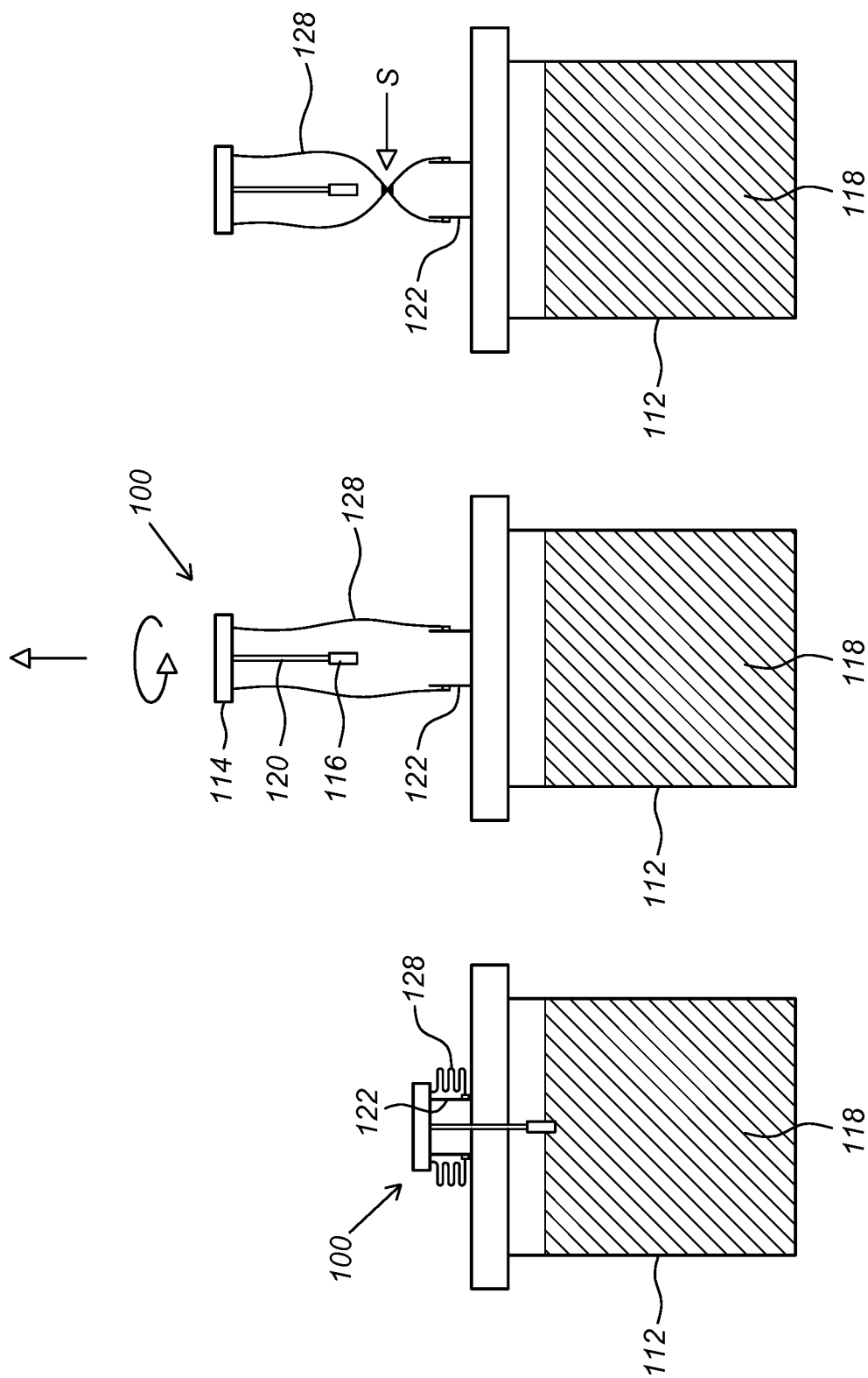

FIG. 2 illustrates an alternate embodiment of a sampler for a bioreactor, including an external container (e.g., sleeve) for receiving a sample portion once withdrawn from the bioreactor.

Figure 3:
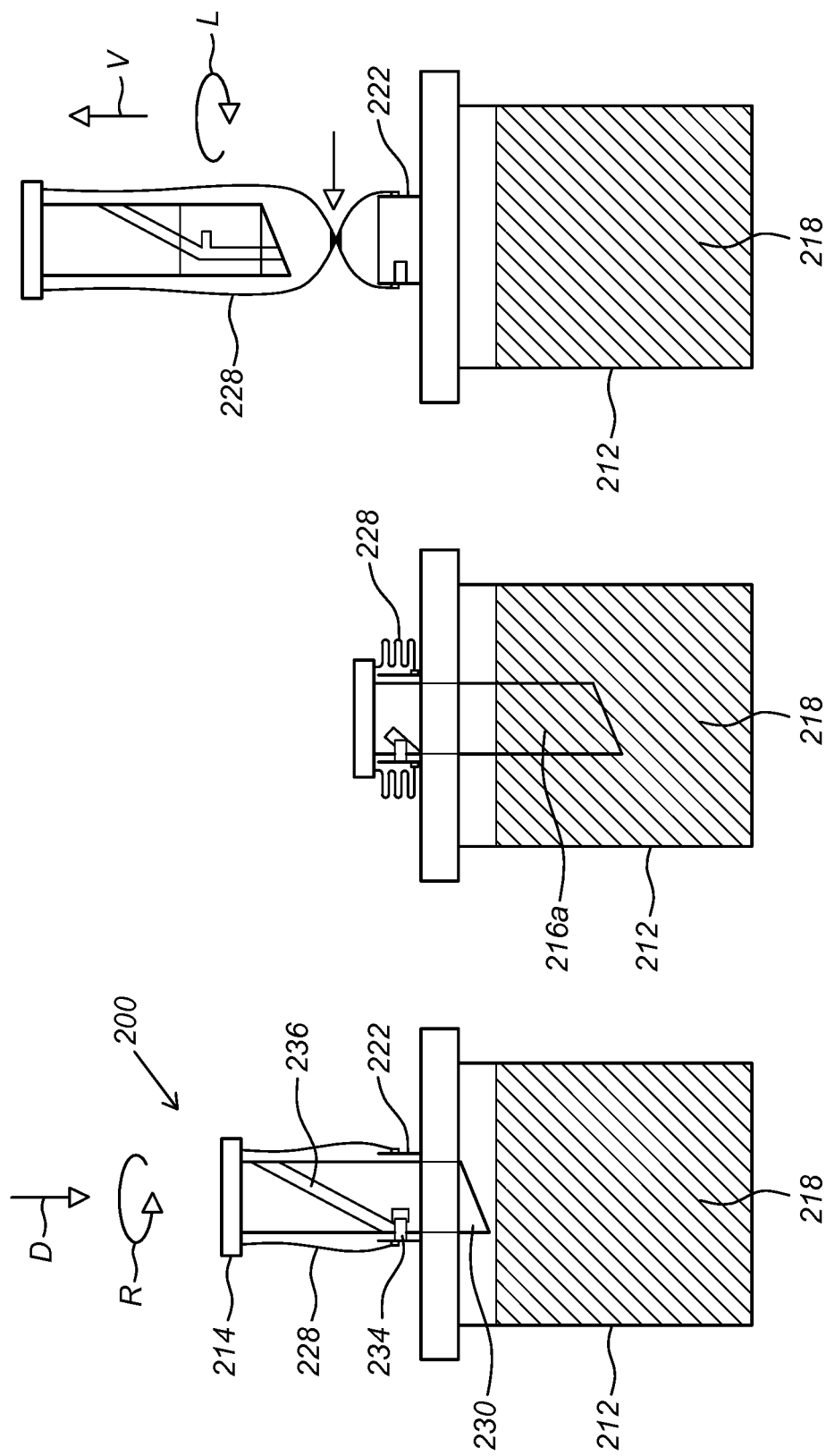

FIG. 3 illustrates yet another embodiment of a sampler for a bioreactor.

FIGS. 3A, 3B, and 3C illustrate a further embodiment of a sampler.

FIGS. 4, 5, and 6 illustrate covers for covering sampling ports on a bioreactor lid.

Figure 7:
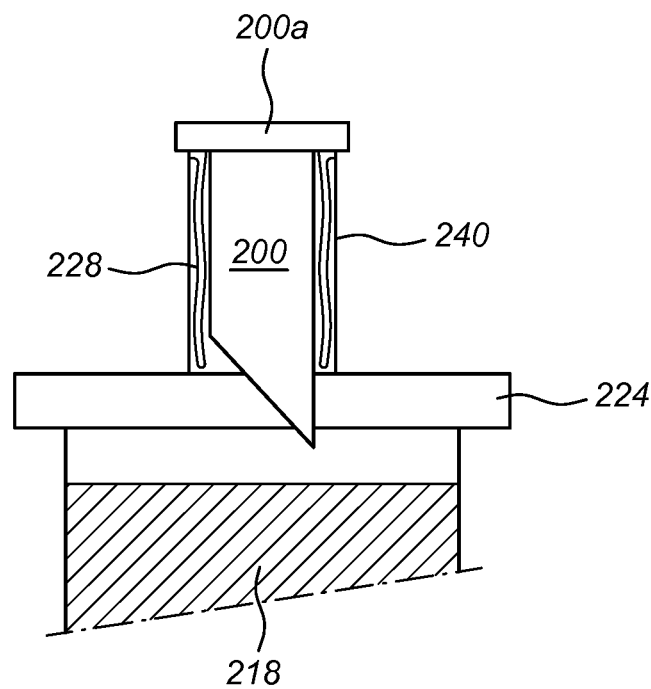
Figure 7:
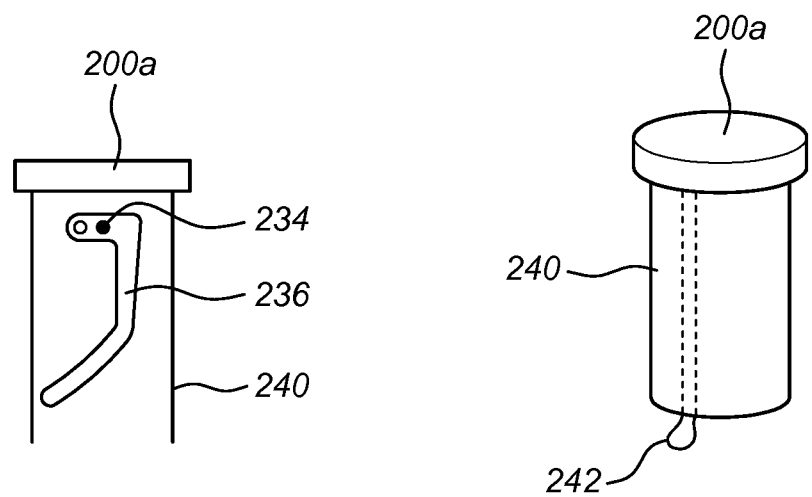
Figure 8:
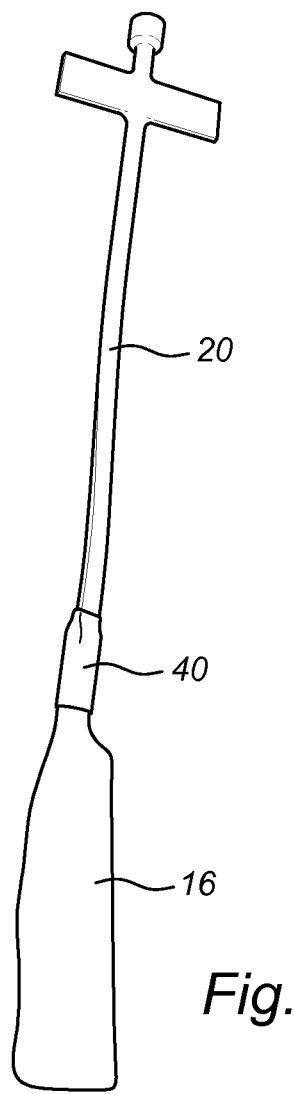
Figure 9:
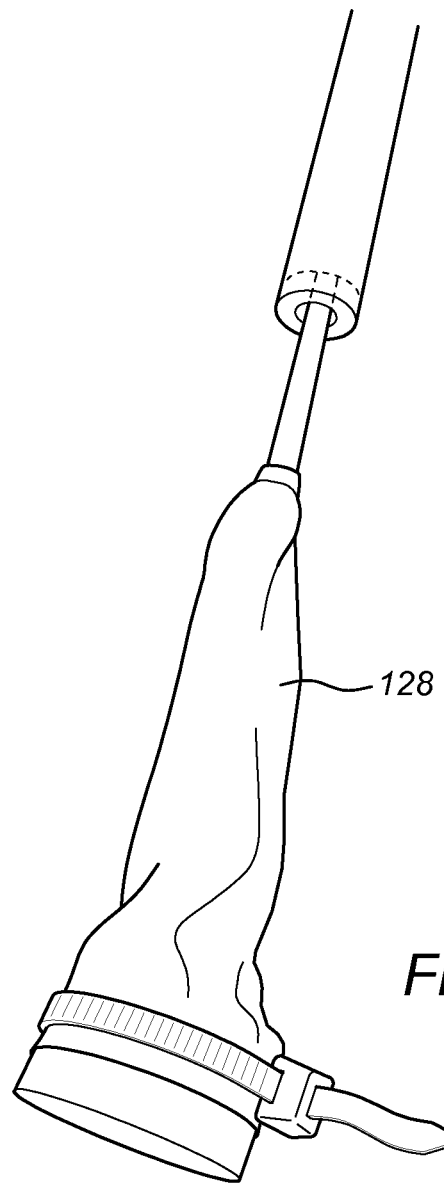

FIGS. 7, 8 and 9 illustrate further aspects of a sampler for a bioreactor.

FIGS. 10, 11, 12, 13, 14A, 14B, 15, 16A, 16B, 17, 18, 19, 20, and 21 illustrate various manners of clamping a sample portion for sampling a cell culture in a bioreactor to a positioner.

Figure 22:
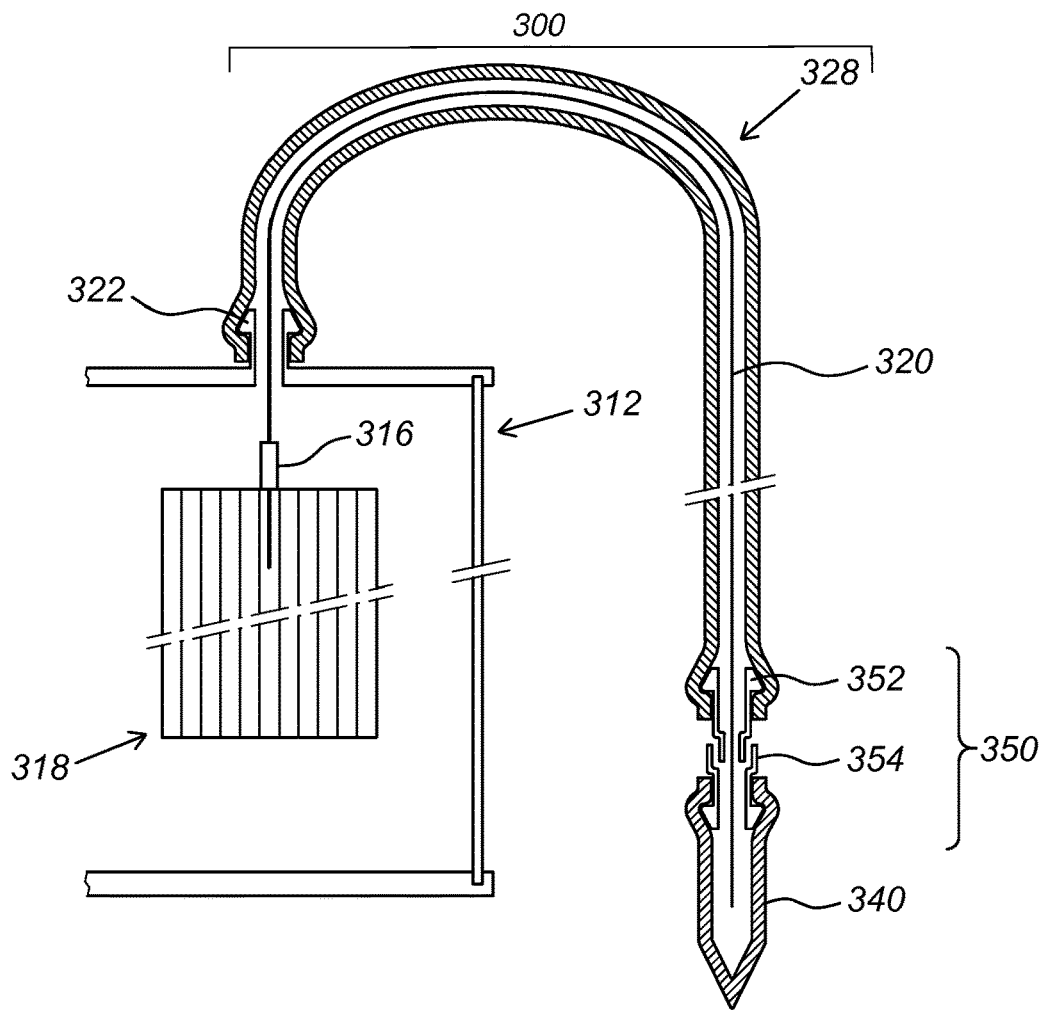
Figure 23:
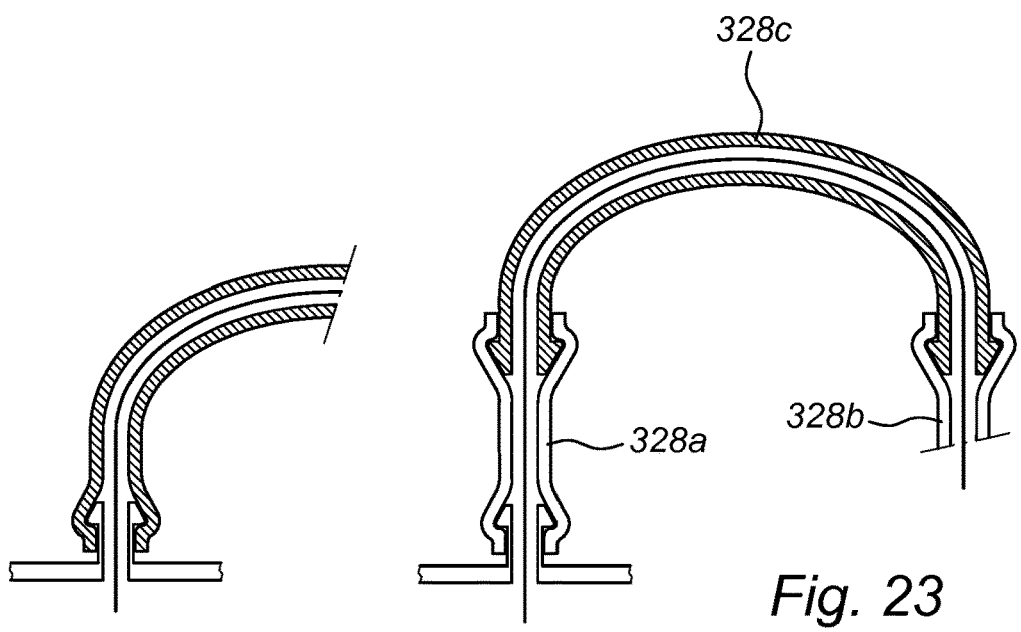

FIGS. 22 and 23 illustrate alternative embodiments of a sampler.

Figure 24:
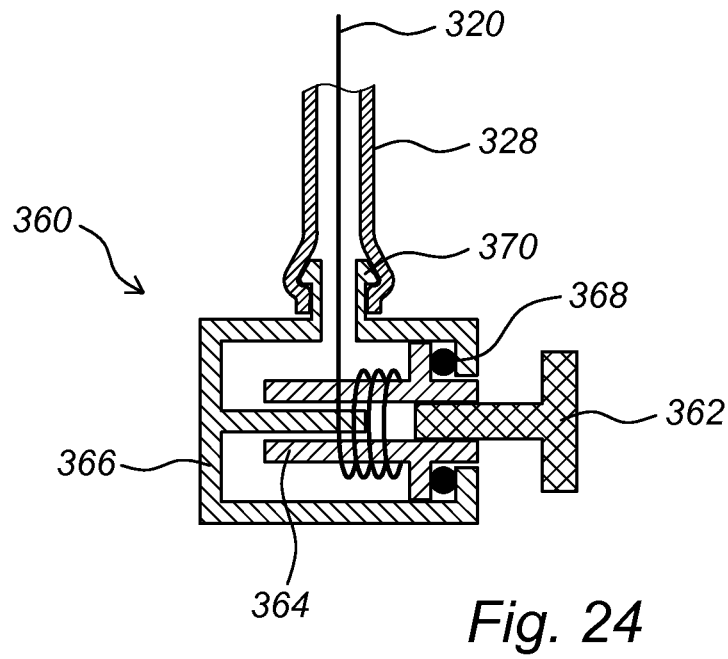

FIG. 24 illustrates one possible embodiment of an actuator for withdrawing a sample portion from a bioreactor.

Figure 25:
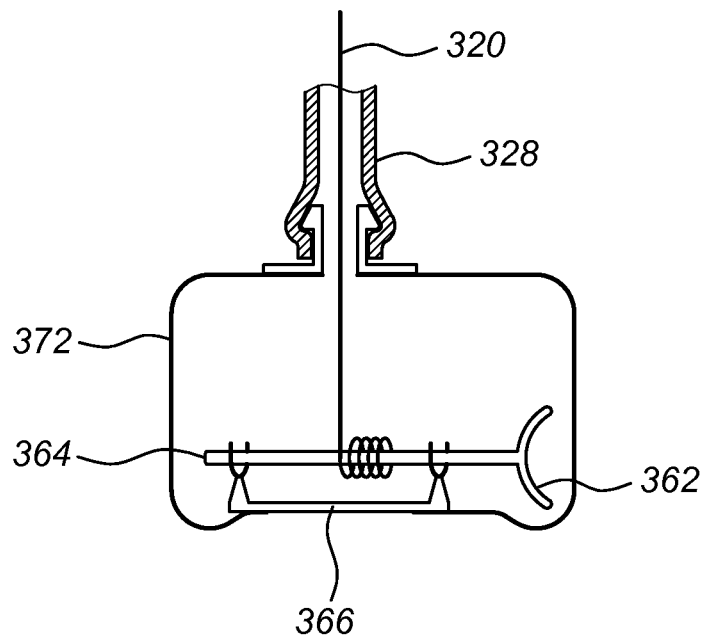
Figure 25:
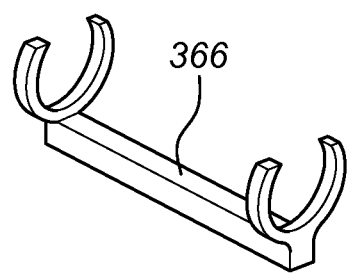

FIG. 25 illustrates another embodiment of an actuator for withdrawing a sample portion from a bioreactor.

Figure 26:
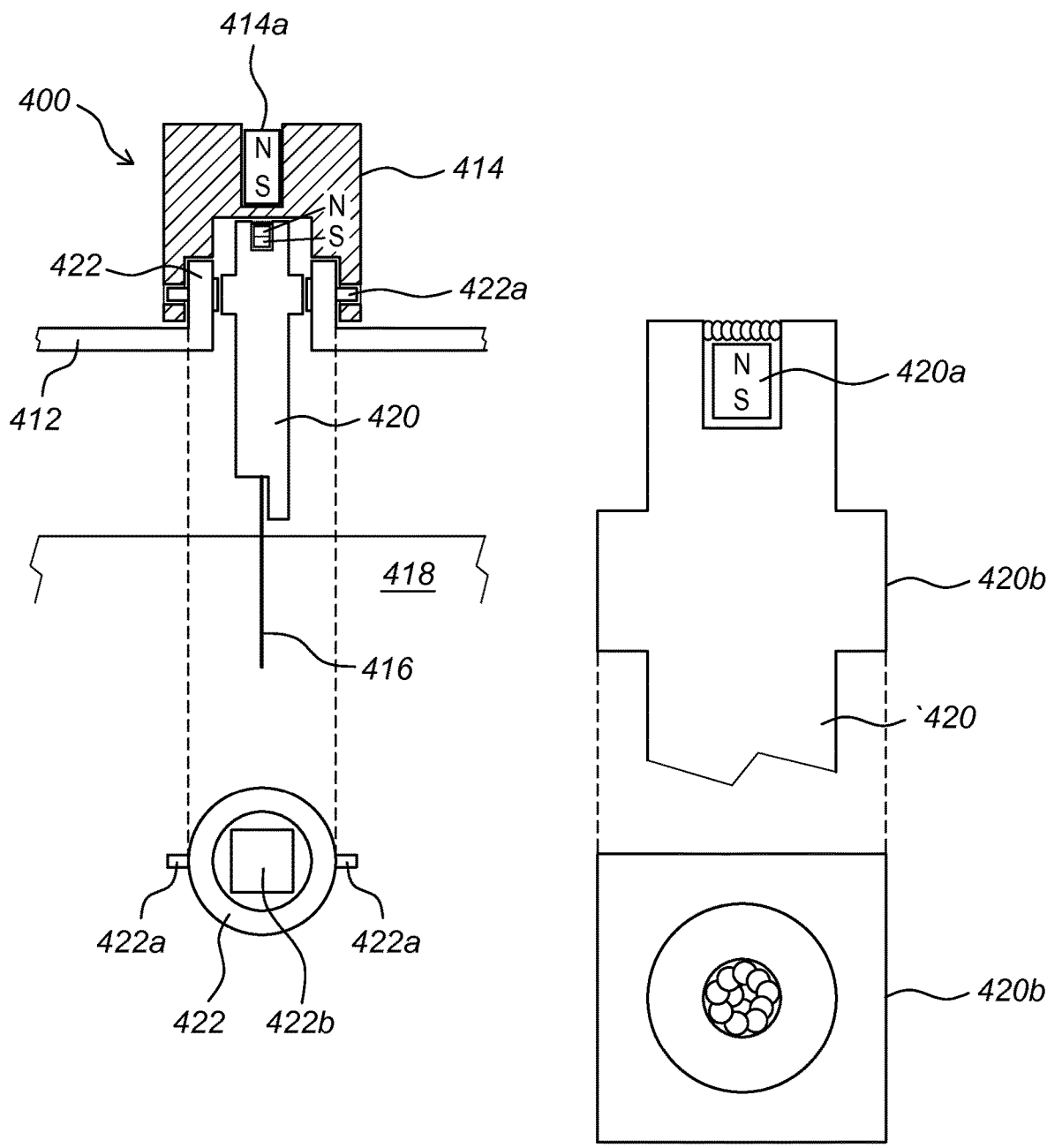

FIG. 26 illustrates an arrangement for connecting a positioner for positioning a sample portion of a bed in a bioreactor to a removable cap of the bioreactor using a non-contact coupling.

Figure 27:
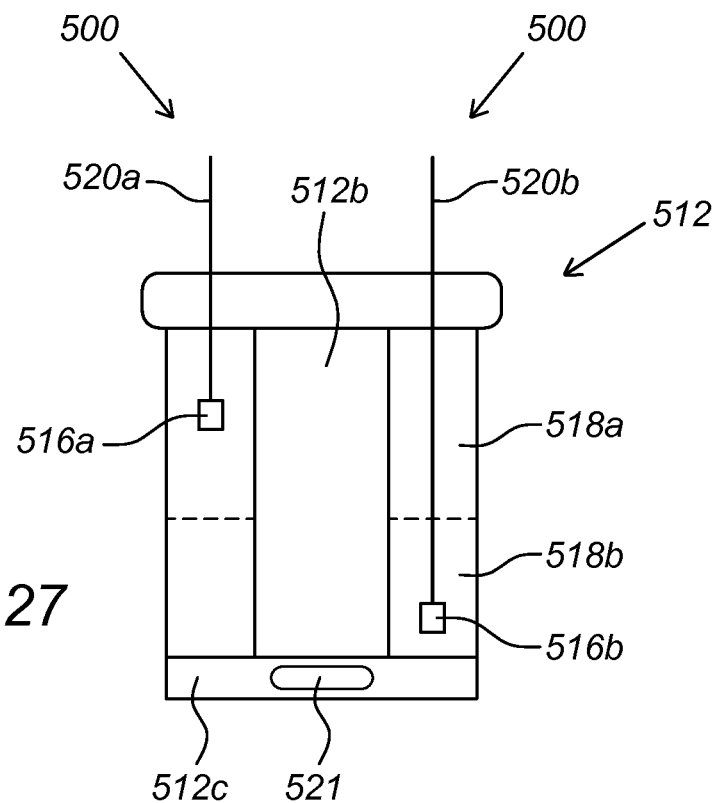
Figure 28:
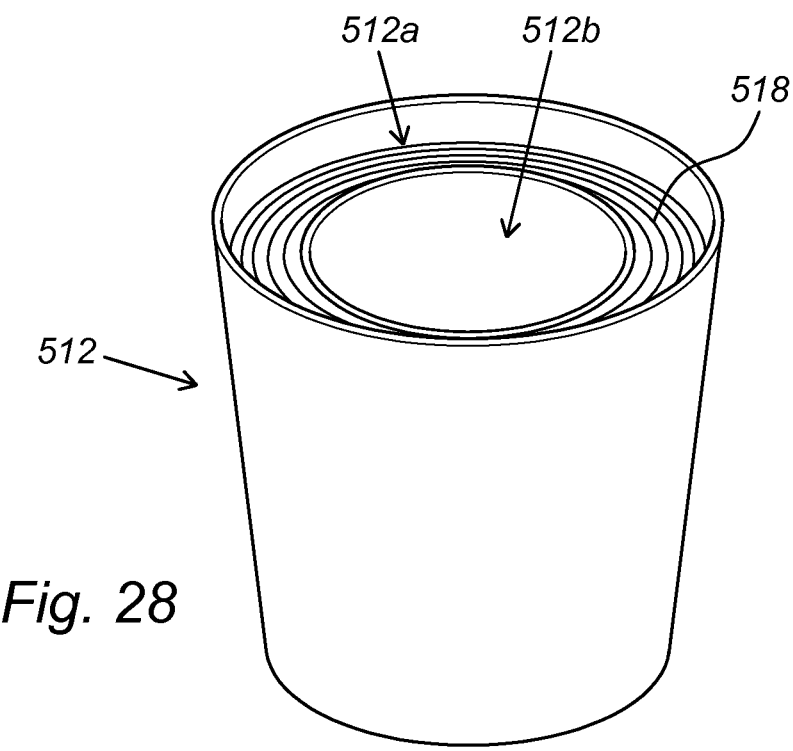

FIGS. 27 and 28 show another possible arrangement of a bioreactor for use with one or more of the disclosed samplers.

Figure 29:
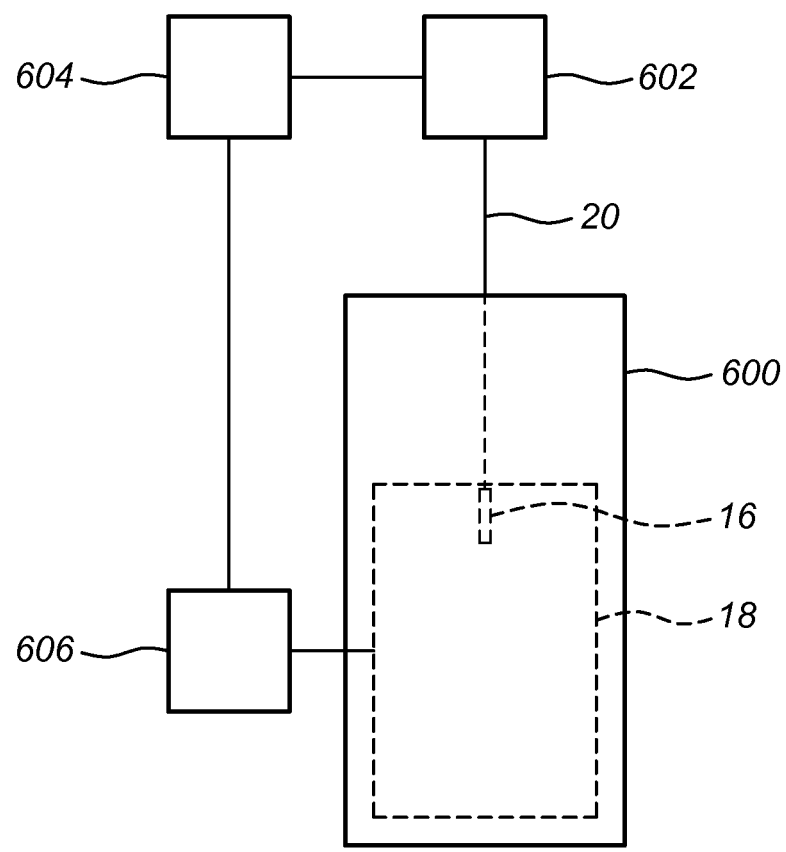

FIG. 29 is a diagram illustrating a control system for a bioreactor including a sampler.

FIGS. 30, 31, 32, 33, 34, 35, 36, 37, 38, 39, and 40 provide illustrations of an exemplary application of a sampler according to the disclosure to a bioreactor.

FIGS. 41, 42, 43, and 44 illustrate various proposals for a sample portion for sampling a cell culture in a fixed bed bioreactor.

Figure 45:
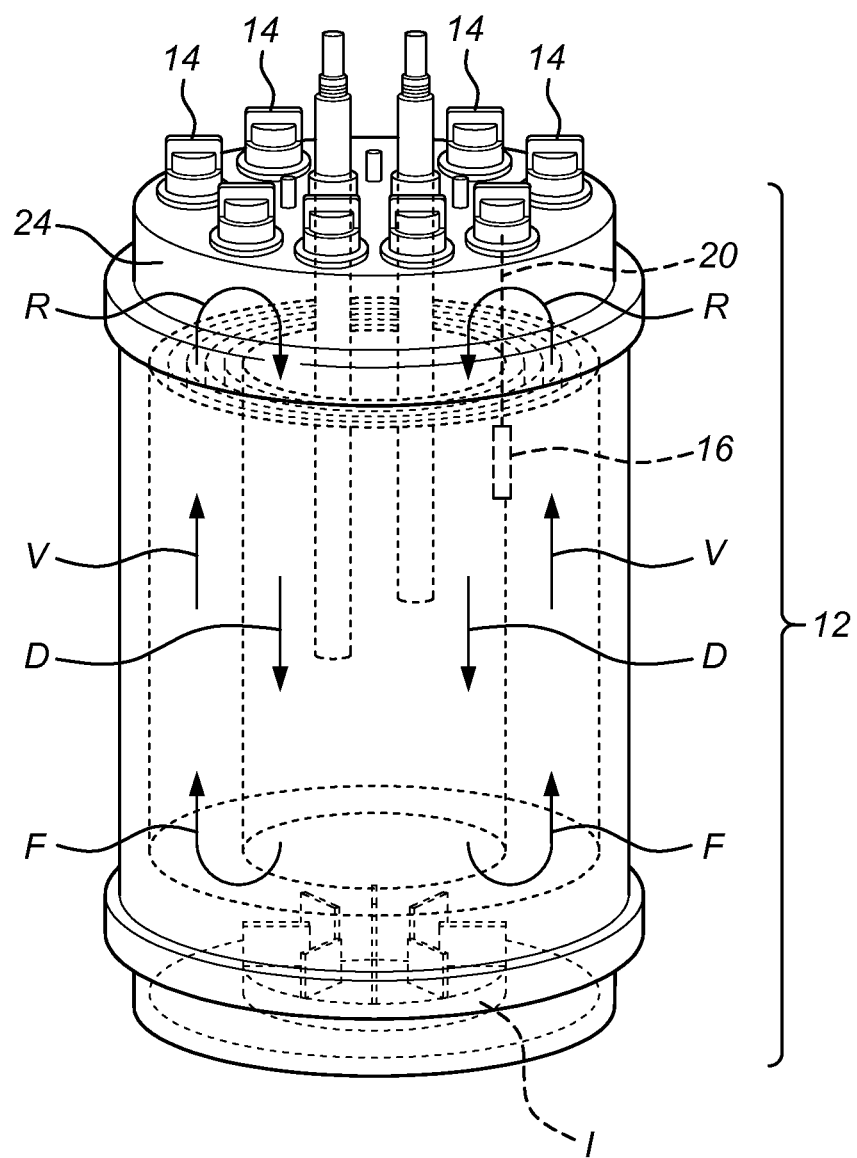

FIG. 45 illustrates one embodiment of a bioreactor to which any of the disclosed embodiments of sampling technology or otherwise may be applied.

DETAILED DESCRIPTION

Reference is now made to FIG. 1, which illustrates a sampler 10 for a cell culture system, such as for example a bioreactor 12, fermenter or the like, according to one aspect of the disclosure. For purposes of this example, the bioreactor 12 is presumed to be in operation under external sterile conditions in a containment unit (such as a laminar flow cabinet, external isolator or the like). However, as outlined further in the description that follows, the sampler 10 may also be used in other environments.

The sampler 10 may comprise a support portion for associating with an opening in the bioreactor 12 providing access to an interior compartment thereof. In the illustrated embodiment, the support portion comprises a cover or cap 14 for sealing the opening in the bioreactor 12, and thus maintains the sterility of the interior compartment, even when not in a containment unit. The support portion may support a removable sample portion 16 for positioning within a fixed bed 18 in the interior compartment of the bioreactor 12.

The sample portion 16 may comprise a substrate (such as, for example, a sheet of material, a sheet of flexible material, or the like, which sheet may be in the form of an elongated strip) which, like the fixed bed itself, is adapted to promote cell growth or cell immobilization/entrapment. The substrate may alternatively comprise one or more fibers, including those arranged as a piece of nonwoven material, as outlined further in the following description. The sample portion 16 may alternatively comprise a portion or part of the fixed bed 18 with perforations, tear away seams or other means for separating from the rest of the fixed bed. Alternatively, the sample portion 16 may be a separate structure for positioning within the fixed bed 18 during the process of assembling the bioreactor 12 (as outlined further in the following discussion). In this case the sample portion 16 may be adapted for detachment and removal from the rest of the fixed bed (such as by providing perforations or tear-away seams in the fixed bed, or pre-cutting the fixed bed or other means for separating samples to create one or more removable (detachable) portions).

The sample portion 16 may be removably attached to a positioner 20 to facilitate holding the sample portion 16 in an appropriate position in the fixed bed 18 and also removing it from the fixed bed 18. Prepositioning of the sample portion 16 within the fixed bed 18 may be achieved by hand via the positioner 20, or by using a tool, such as tweezers (not shown) to pass the sample portion 16 into the fixed bed 18 through a port 22 in the lid 24 of the bioreactor 12 (or by removing the lid entirely). This may be done prior to the commencement of the bioprocessing operation, even during assembly of the bioreactor or manufacturing and assembly of the fixed bed.

The fixed bed 18 may comprise any substrate for achieving cell growth or cell immobilization, and may comprise, for example, a structured fixed bed (which means that it is formed of an easily replicated, generally homogeneous, substantially fixed structure, and thus is not randomly oriented or unstructured, yet, as can be appreciated, could take a variety of sizes or shapes while meeting this qualification). The material of the fixed bed 18 may be woven, non-woven, a fiber matrix, or other forms, and may be formed of various polymer materials, including but not limited to polyethylene and polyethylene terephthalate. In one embodiment, as shown in a top view in FIG. 1A, the structured fixed bed comprises a non-woven material 18a arranged in at least two layers on and within which cells grow. These layers are thus considered cell immobilization layers. In the particular form shown, the non-woven material 18a is arranged in a rolled or spiral fashion, with each of the two cell immobilization layers separated by spacer layers 18b, which promote culture and media flow between the various layers. The sample portion 16 may be a pre-defined portion of a cell immobilization layer. It may be a separate substrate positioned (as shown) between two of the layers of the bed 18 in rolled or spiral form, such as cell immobilization (or non-woven material) layers 18a. Alternatively, the sample portion may be located between a spacer layer and an adjacent cell immobilization layer. The fixed bed 18 may have only a single cell immobilization layer alternatively in roll or spiral with a single spacer layer.

However, the above is merely one example, and is not intended to limit the manner in which the sample portion 16 may be associated with a fixed bed 18 of any known form (e.g., positioning within a fiber matrix, or an arrangement of layers that is not spirally wound as shown). For instance, FIG. 1B illustrates a non-structured fixed bed, which may comprise a plurality of randomly oriented fibers 18c. In this embodiment, the sample portion 16 may comprise one of the fibers 18c. This fiber 18c may be connected to the positioner 20, as indicated (or as a substrate of non-woven fibers). Alternatively, more than one fiber can be connected to the positioner 20 and act as the sample portion (such as a non-woven material, as noted previously).

While FIG. 1A illustrates a rolled, generally cylindrical arrangement for a structured fixed bed 18 with at least two layers (including a cell immobilization and spacer layers 18a, 18b), it should be appreciated that other forms may be used. Thus, with reference to FIG. 1C, the fixed bed 18 may comprise a plurality of concentric layers 18a that are continuous, and may be in any shape (e.g., circular, square). Alternatively, the layers 18a may be linear. In any of these cases, spacer layers 18b may or may not be provided, and the sampler portion 16 may be located at any location (or locations) within the bed 18, without limitation, depending on the desired approach to sampling.

Returning to FIG. 1, an anchorage point, such as a sidewall of the port 22 associated with the lid 24 of the bioreactor 12, may be adapted to form a seal with the cover or cap 14 to ensure that sterility is maintained. The cap 14 may be releasably connected to the port 22. This may be achieved by threading or other means of secure, but releasable connection (e.g, a bayonet fitting, as outlined further in the following description, or a door with a releasable latch (push-pull type of arrangement, or even a friction or interference fit)).

To ensure that cell growth is achieved on the sample portion 16 in the illustrated format, the positioner 20 may extend a distance sufficient to ensure that the sample portion 16 is at least partially positioned within the fixed bed 18. As can be appreciated, this distance may vary depending on the size and shape of the bioreactor 12, as well as the desired location for the sampling to occur, the type of bed, or the type of culture. The positioner 20 may be connected to the cover or cap 14 serving as the support, but may also be separate therefrom (such that the cap 14 may be removed while the positioner 20 remains in position, and can then be withdrawn and the cap replaced). The former version may be applied more readily to a non-structured fixed bed, such as shown in FIG. 1B, which allows the positioner 20 to be passed through the port 22 for positioning in the non-structured material within the non-structured bed. A structured fixed bed is more suited for the latter version, since the sample portion 16 may be pre-positioned within the structured fixed bed layers and held therein, and the positioner 20 later associated with the cap 14 (if desired).

In any disclosed embodiment, the spacer layers and/or the cell immobilization layers which make up respectively the spacer section and the immobilization section in the matrix assembly are preferably made of a biocompatible polymer selected from polyester, polyethylene, polypropylene, polyamide, plasma treated polyethylene, plasma treated polyester, plasma treated polypropylene or plasma treated polyamide. Said layers can be hydrophilic or hydrophobic. The cell immobilization layers are preferably hydrophilic.

The thickness of both layers will advantageously be between 0.05 mm and 3 mm, more preferably between 0.1 and 2 mm or between 0.1 and 1 mm. Suitable material for the cell immobilization layer may be a woven or nonwoven material. By preference, a nonwoven material is used. A nonwoven, contrary to a woven material, is a fabric which is not created by weaving or knitting and does not require converting the fibers to yarn. Nonwovens are broadly defined as sheet or web structures bonded together by entangling fiber or filaments (and by perforating films) mechanically, thermally or chemically. The nature of the nonwoven material used in the current application may be of any origin, either comprising of natural fibers or synthetic fibers. By preference, the nonwoven is made of a polymer, such as polyester or polypropylene. The cell immobilization layers used in the current invention may be chosen from a polyethyletetereptahalate nonwoven. The nonwoven material may be plasma treated to enhance cell adherence and flow.

The spacer layers may consist of a (biocompatible) polymer with mesh size as described above. In one embodiment, the spacer layer is a synthetic woven fabric or structure. In another embodiment, the spacer layer is a bearing structure. Such structure may be produced from a biopolymer (e.g. alginate). Other suitable material for this purpose is silica, polystyrene, agarose, styrene divinylbenzene, polyacrylonitrile or latex. The spacer layer may be gamma irradiated in order to reduce bioburden.

The design of the matrix assembly can take many forms depending on the application and type of bioreactor. In an embodiment of the current invention, the immobilization section and spacer section are alternately positioned. Alternately positioned means that each spacer section is followed by a cell immobilization section which is itself followed by a spacer section. The alternately positioned sections may alternate in vertical position as shown in the figures (see further) or in a horizontal position according to the use of the matrix and/or to the bioreactor in which the matrix will be introduced. In this embodiment, one or more layers of cell immobilization layers are superimposed on one or more spacer layers (or vice versa). This configuration may be repeated several times if deemed required in order creating a stack of several immobilization and spacer sections. Ideally, the end configuration may comprise between 1 and 500 alternations of the above described layering. The stacked layers may be positioned in a frame or cassette or sealed/connected at their circumference. In another embodiment, the achieved stack can be rolled around an axis or core to achieve a spiral configuration.

The number of layers used in both the immobilization section and spacer section can be chosen based on the application, characteristics of the layers (dimensions, size, etc.) and desired result. Hence, the number of layers within either immobilization section or spacer section may be between 1 and 20, more preferably between 1 and 10, even more preferably between 1 and 5.

As mentioned, the presence of the spacer sections creates space inside the matrix through which the culture medium flows. This provides improved circulation of the culture medium through the matrix thereby reaching all cultured cells. This effect is even more enhanced in the embodiment wherein the spacer section comprises one spacer layer and the immobilization section comprises two immobilization layers. The culture medium flowing inside the matrix via the spacer sections is tangentially oriented with respect to the cell immobilization sections.

Examples of releasable connections between the positioner 20 and the support for it (cap 14) are shown in FIGS. 1D, 1E, and 1F. In FIG. 1D, the cap 14 includes flexible projections 14 *a* forming a receiver 14 *b* for receiving and retaining a portion 21 of the positioner 20 (which portion 21 may also form part of a separate structure, such as a sleeve). As can be appreciated, the portion 21 within the receiver 14 *b* is retained against movement in an axial direction of the positioner 20 unless sufficient force is generated to separate the projections, yet allows for free rotation. Hence, the cap 14 may be rotated for removal (if a bayonet or threaded connection) without causing the positioner 20, and hence the sample portion 16, to rotate relative to the fixed bed 18, which might cause an undesirable disruption or result. The cap 14 can still be withdrawn in the vertical direction, though, including with the positioner 20 remaining attached, or separated therefrom (in which case it can be accessed and removed independently of the cap). Likewise, the positioner 20 with the sample portion 16 may be positioned in the bioreactor 12, and the cap 14 then connected to the positioner 20. Of course, the arrangement could also be reversed, such that the projections are on the sleeve/positioner, and the portion for engagement is on the positioner.

FIG. 1E illustrates a version in which a removable part 14 *c* includes the projections 14 *a* forming the receiver 14 *b*. Fasteners, such as screws 14 *d*, clips, or snaps, may be used to secure the part 14 *c* to the cap 14. Using this arrangement, the part 14 *c* may be released before the cap 14 is removed, and the cap 14 may be associated with part 14 *c* once in place. Seals, such as O-rings 14 *e*, may also be provided for sealing the interface created with the exterior environment through the openings for the fasteners/screws 14 *d*.

FIG. 1F illustrates another version in which the part 14 *c* is adapted for passing through an opening O in the cap 14. An external fastener, such as a threaded nut 14 *f* may then be used to secure the detachable part 14 *c* to the cap 14, such as by threading along a shank 14 *g* thereof. In this manner, the part 14 *c* may be selectively associated with the cap 14 during placement or removal, and without disturbing the position of the positioner 20 and sample portion 16.

As indicated, cells may be cultured in the fixed bed 18, as well as on the sample portion 16 as a result of its positioning. When external examination of the cell growth is desired, the sample portion 16 may be removed from its location in the fixed bed 18. In one example, this may be achieved by removing the cap 14 from the port 22. This removal is shown in FIG. 1 as involving rotation of the cap 14 in one direction (note arrow R) to release a connection (as discussed below), and then raising it in a vertical direction V. Port 22 could also be associated with a sidewall of the bioreactor 12 or any other part, in which case the movement would be primarily horizontal. Likewise, the cap or cover 14 could also form a friction fit with an associated part of the bioreactor 12, such as the port 22 or another part of the lid 24 for providing access to the fixed bed 18, in which case only vertical movement may be used to remove the cover 14.

The positioner 20 may be removed from bioreactor 12 as well to recover the sample portion 16 from the fixed bed 18, without requiring an enhanced level of coordination or dexterity, and without the need for using a tool that can disrupt the surrounding material of the fixed bed 18. Examination of the sample portion 16 may then be done external to the bioreactor 12 to evaluate the cells thereon, which would be directly representative of the corresponding cell growth in the fixed bed 18. Optionally, a second cover or cap 26 may then be used to seal port 22, and a new sample portion 16 may also be positioned within the fixed bed 18 via an associated positioner in case a desire exists to repeat the sampling operation.

Turning to FIG. 2, a second embodiment of the sampler 100 is shown, for possible use in environments where the bioreactor 112 is internally sterile, but the external environment is not sterile (e.g., where the bioreactor 112 is of a large scale or size, making use of a conventional isolator or cabinet difficult, costly or impossible). In this case, the sample portion 116 (as well as the bioreactor 112) must be protected against contamination during removal and prior to inspection of the sample portion.

In this embodiment for maintaining the sterile conditions, the basic parts are essentially the same as above, but an additional partition or barrier, optionally in the form of a flexible sleeve 128, is provided. This sleeve 128 forms a sterile barrier between the anchorage point, such as port 122, and the cover or cap 114. This sleeve 128 may be formed of an elongated piece of flexible material, such as a thin, flexible polymer material, and may be arranged so as to not interfere with the connection between the cap 114 and the port 122.

When it is desired to take a sample of the fixed bed 118 during the culturing process, the cap 114 is released and removed. Consequently, the sample portion 116 is withdrawn from the fixed bed 118 via positioner 120, but remains under sterile conditions as a result of the surrounding sleeve 128 and the seals established with cap and port. A portion of the sleeve 128 may then be sealed, either mechanically or by welding (e.g., using heat), as indicated by arrow S in FIG. 2, which also seals a remaining portion of the sleeve for covering the opening to the bioreactor 112 (e.g. port 122). Other examples of sealing means in the form of an aseptic connection include the Quickseal or Clipster technologies distributed by Sartorius (see, e.g., U.S. Patent Application Publication Nos. 2012/0017733 and 2011/0155274, the disclosures of which is incorporated herein by reference), or a mechanical seal between inner portions of the sleeve 128 could be provided, similar to a "Zip-Lock" style of resealable, flexible bag. In any case, the sample portion 116 remains under sterile conditions in a compartment thus formed as a result of the severing/sealing of the sleeve, yet can be transported for further examination or processing, and the contents of the bioreactor 112 also remain under sterile conditions with the cap or cover replaced. In situations where the external environment is sterile, then the sleeve 128 may be omitted, yet the same parts used to perform sampling in the desired manner.

It is sometimes desirable to sample a portion of the fixed bed itself, such as by cutting it out and extracting it—at the end of a cell culture process when more cells are needed for sampling. One could attempt to add material or the number of fibers to the sample portion to increase the number of cells available for analysis in a sample. However, achieving the required scale may be difficult using this methodology. In this regard, a third embodiment of the sampler 200, which is shown in FIG. 3, may receive and recover or extract a relatively larger sample portion 216a of the fixed bed 218 in order to more effectively harvest a larger number of cells. In the illustrated embodiment, the sample portion 216 is connected to the cover or cap 214 associated with a port 222.

In one embodiment, the sampler 200 includes a cutter 230 at one end portion for engaging with a portion of the fixed bed 218 to sever or detach it and form the sample portion 216a. The distal end of the cutter 230 may be adapted for cutting the material of the fixed bed 218, and may have a pointed end, blade, or both, essentially like a needle, and the interior of the sampler 200 may be at least partially tubular or hollow for capturing the portion of the fixed bed 218 and removing it once detached. Initially, the cutter 230 may be held in a position at least partially within the bioreactor 212, but spaced from the fixed bed 218, such as by retainer in the form of a locking pin 234. The locking pin 234 may associate with a rail or channel 236 of the cutter 230 extending generally in a direction corresponding to the direction of relative movement with the bioreactor 212.

The sample portion 216a may be used in a situation where the bioreactor 212 is in a sterile environment, but may otherwise include a sleeve 228 for maintaining such an environment in the space surrounding the cutter 230. When it is desired to remove a sample of the fixed bed 218, the cutter 230 may be manipulated such that the locking pin 234 (shown at the home position) travels within the channel 236 until the cutter 230 at least partially plunged into the material of the fixed bed 218 (note down arrow D and rotational arrow R), thus capturing a "core" sample of the fixed bed in an interior hollow compartment of the cutter 230. As can be appreciated, the travel distance of the cutter 230 may be regulated by simply altering the dimensions and geometry of the channel or groove 236. The cutter 230 may then be withdrawn from the port 222 (up arrow U and opposite rotation arrow L, but again the movement could be up only in the event of a different connection, such as a friction fit), and the sleeve 228 severed/sealed in the manner described above to maintain the sterile condition (both with respect to the cutter 230 and the bioreactor 212).

In another possible version, as shown in FIG. 3A, the sampler 200 may be pre-positioned within the fixed bed 218 (structured or otherwise). Within its interior, the sampler 200 may include a pre-cut or pre-assembled substrate or material (e.g., a nonwoven material) serving as a sample portion 216 for entrapping or growing cells, and thus the body 220 of the sampler may function as a positioner (similar to positioner 20 of sampler 10). The material forming the body 220 of the sampler 200 may include perforations P to allow for cell culture fluid to flow into the interior of the body and thus to any cells entrapped or grown on the material of the sample portion 216. Removal of the sample portion 216 from the fixed bed 218 may be done in the manner shown in FIG. 3, if maintaining sterility is required, or in any other manner shown herein.

Still another option is for the FIG. 3 version to be used without providing a cutter 230 on the sampler 200, as shown in the side and top views FIGS. 3B and 3C. Rather, a portion of the fixed bed 218 may be pre-positioned and adapted for removal as the sample portion 216 when received in the interior of the sampler 200. The interior of the body of the sampler 200 may include grippers, barbs or other engaging structures to engage and remove the sample portion 216 Again, sterile conditions may be maintained by using the sleeve 228 shown in FIG. 3.

FIGS. 4-5 illustrate one exemplary embodiment of the cover or cap 14 (or 114, 214) for use in connection with the port 22 (or 122, 222). The cap 14 may include a labyrinth (e.g., L-shaped, X-shaped, S-shaped, or like serpentine) slot 15 for mating with a corresponding post 22a extending radially from an upstanding portion of the port 22, and thus form a releasable bayonet-style fitting. The cap 14 may also include a tab 17 to facilitate manual grasping for removal, and may be reusable/resealable. As can be appreciated, a plurality of these caps 14 may be provided on a single lid 24 to create a variety of sampling options at different locations within the fixed bed, as shown in FIG. 6.

Referring to FIG. 7, and using the FIG. 3 embodiment as an example, an arrangement for a temporary support 240 associated with a port 222 in the bioreactor lid 224 is illustrated. The support 240 is arranged to receive the sampler 200, which includes an oversized head 200a for engaging the support 240. The sleeve 228 is connected between the bioreactor lid 224 and the sampler 200, such as along the underside surface of the oversized head 216a. The pin 234 and groove 236 from FIG. 3 can also be seen, which correspond to the sampler 200 in the home or raised configuration.

When it is desired to sample the fixed bed 218, the support 240 may be removed to allow for the sampler 200 to advance. This may be achieved by cutting through the sidewall, but in one particular embodiment, a frangible connection is established by a pull 242 embedded in the sidewall that, when manipulated, breaks the corresponding connection between portions of the support 240 along a vertical line. This allows for the support 240 to be removed from the supporting position, and the sampler 200 may then be used as per the indication in FIG. 2, yet reliable support is provided for the sample portion prior to use and the sterile conditions are fully maintained. Instead of a pull 242, other forms of frangible connections may also be used, such as for example a perforated tear line, zipper, latch and hinge (living or otherwise), or other similar arrangements.

FIG. 8 shows an embodiment of the sample portion 16 of the FIG. 1 embodiment, and the positioner 20, which is shown as being an elongated rod-like structure. The sample portion 16 may comprise the same or a similar material as the material of the fixed bed 18, such as a nonwoven fabric of one or more fibers. In a simple form, as shown in FIG. 8, the sample portion 16 may be temporarily affixed to the positioner 20 using a fastener, such as a crimped piece of metal 40 (see, e.g. FIG. 16) to form a secure connection. While shown having a generally rectangular shape, the sample portion 16 in this or any embodiment may comprise any shape, thickness or dimension. This would permit cell association therewith in relation to the cell density of the entire fixed bed, without limitation. As shown in FIG. 9, the positioner 20 may also be associated with the sleeve 128, which as described above may be connected to the port of the bioreactor (not shown).

Figure 10:
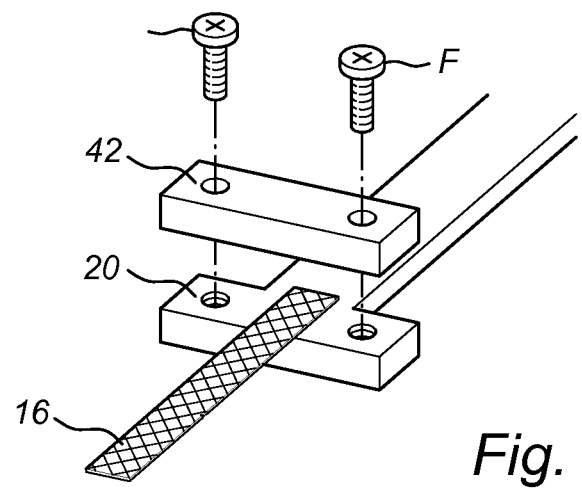
Figure 11:
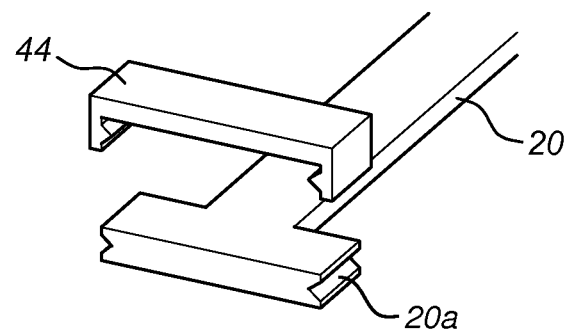
Figure 12:
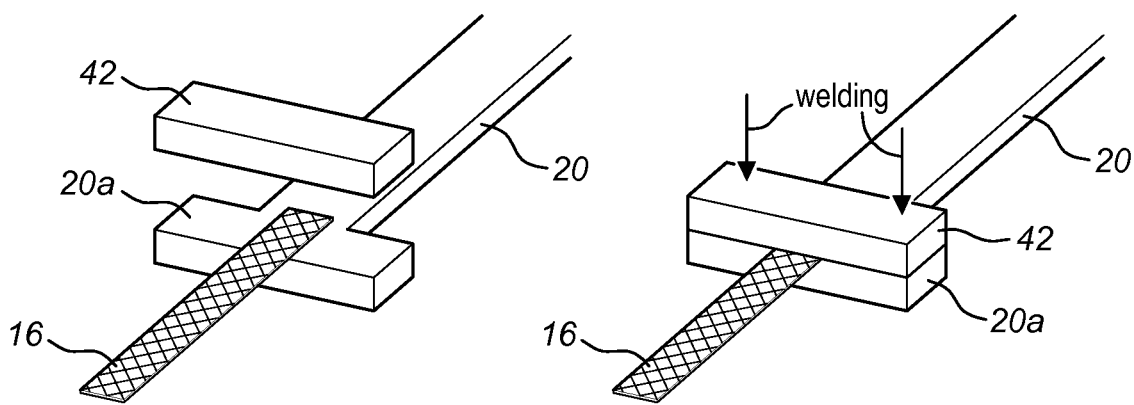
Figure 13:
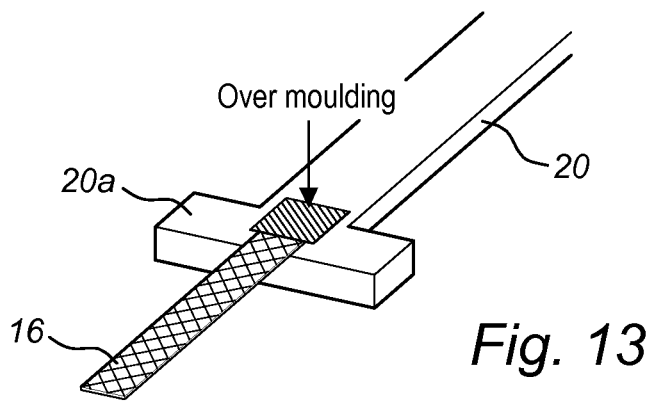
Figure 14:
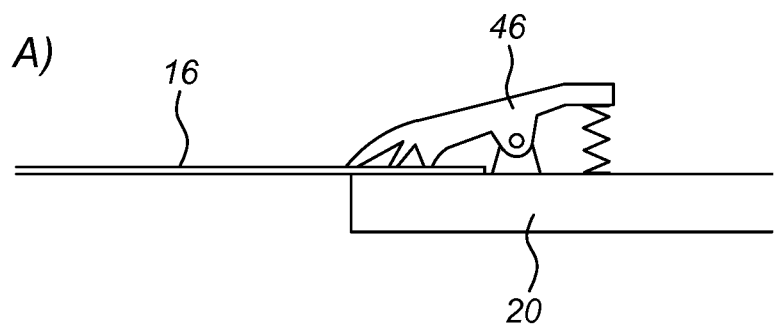
Figure 15:
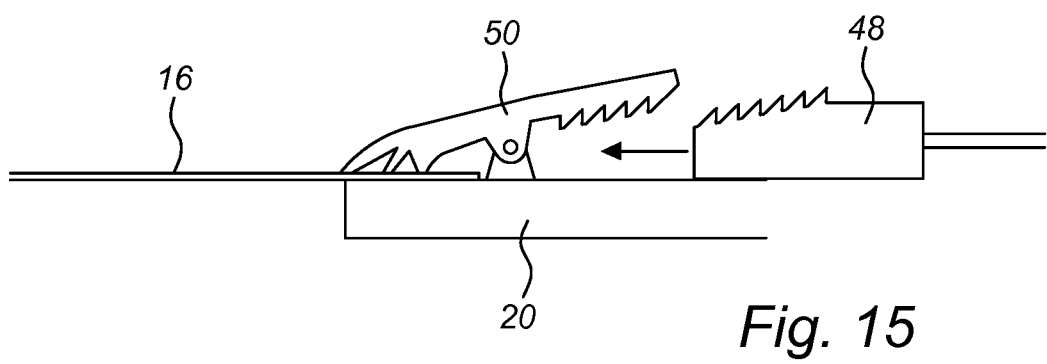

As indicated above, the sample portion 16 may be removably attached to the positioner 20 in a variety of ways, but which may be characterized as forming a clamp for clamping the two structures together. As shown in FIG. 10, a distal end of the positioner 20 may comprise a removable portion 42 that may be fastened in place by fasteners F passing through the parts to sandwich a portion of the sample portion 16 therebetween. FIG. 11 shows an embodiment in which a clip 44 is clipped over the sample portion (not shown) and an oversized distal end portion 20a of the positioner 20, which may be T-shaped. FIG. 12 shows that the portion 42 may be secured to the positioner 20 by welding or adhering (e.g., gluing), rather than via removable fasteners. FIG. 13 shows that the sample portion 16 could be molded directly to a distal end of the positioner 20, such as by overmolding. A spring clamp 46 may also be used to clip the sample portion 16 to the positioner 20 as shown in FIG. 14, and the arrangement of FIG. 15 uses a toothed wedge 48 and a pivotable clamp 50 to hold the sample portion 16 in place.

Figure 16:
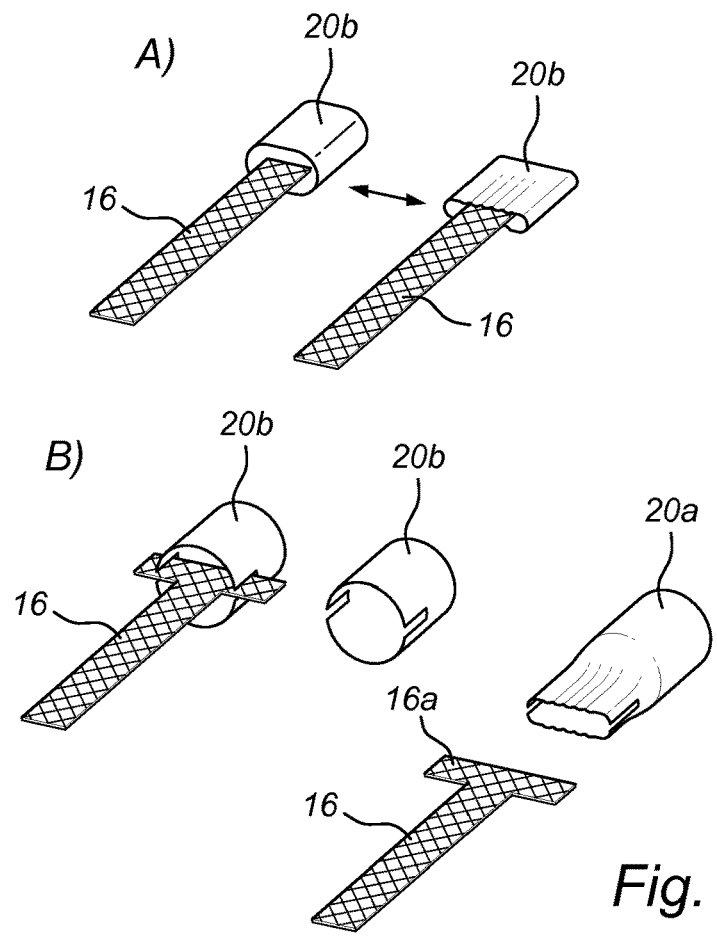
Figure 17:
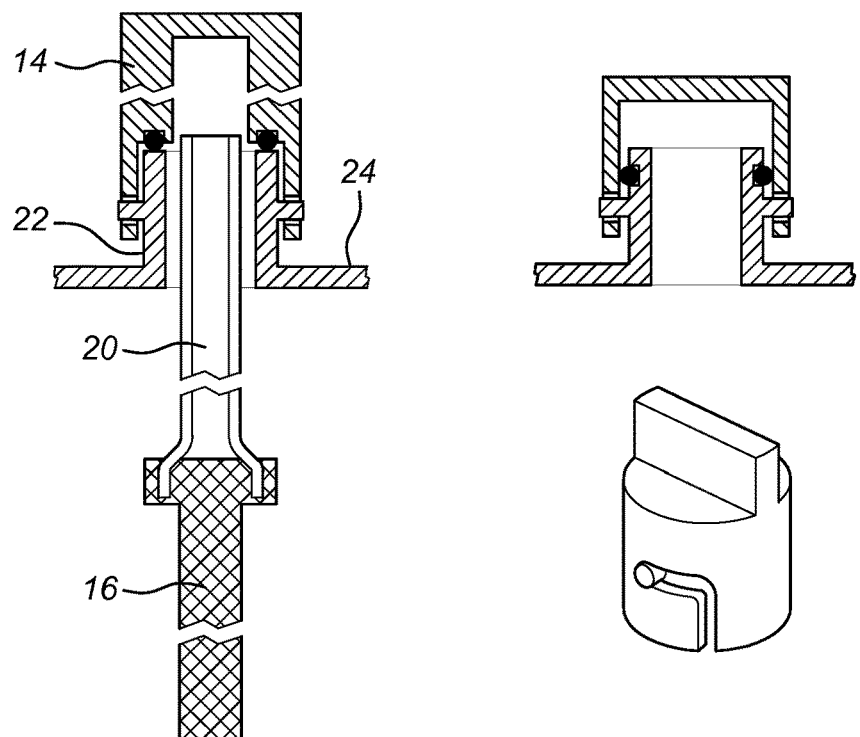
Figure 18:
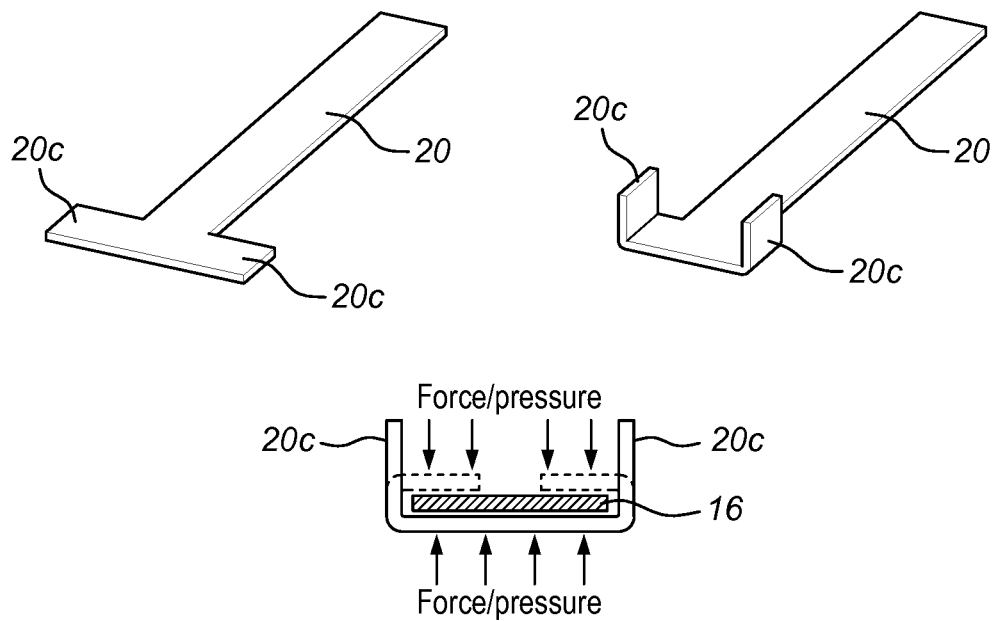
Figure 19:
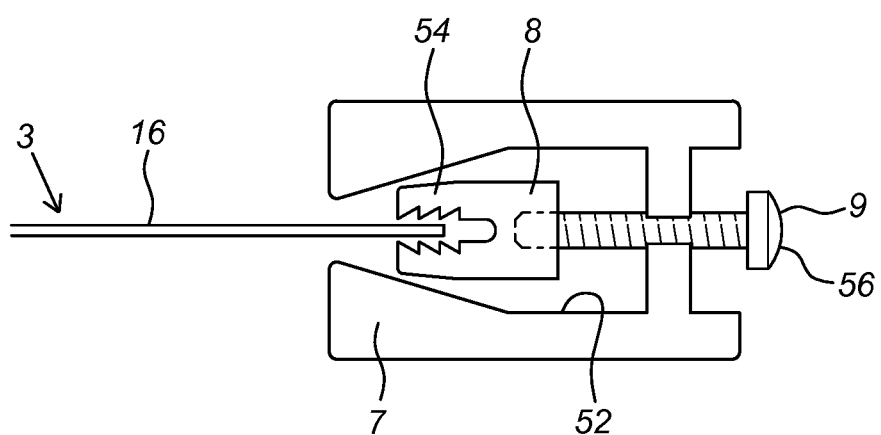
Figure 20:
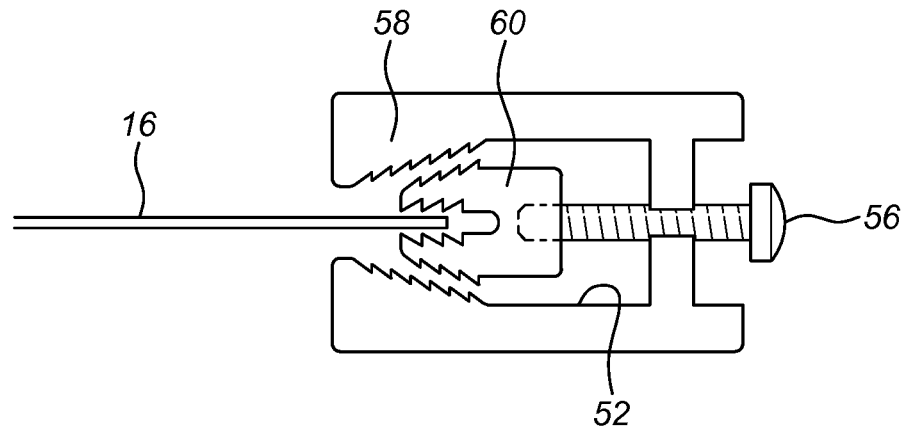
Figure 21:
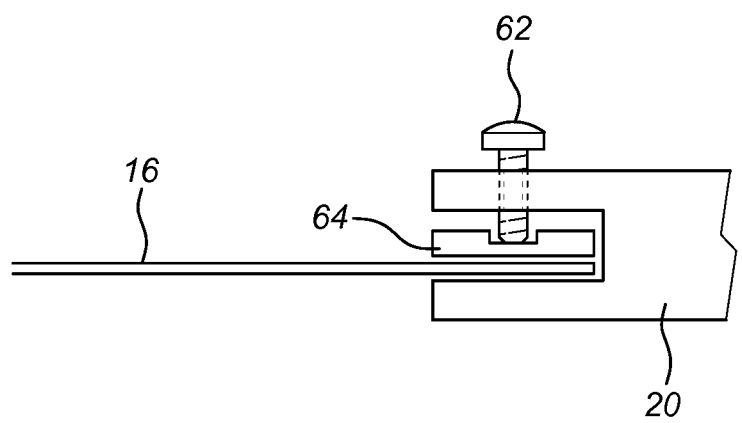

In a further example, FIG. 16 shows that the positioner 20 may be provided with a clamp in the form of a malleable end 20b (e.g., formed of Aluminum or other soft material) and clamped onto the sample portion 16 (which may have an oversized head 16a to facilitate the connection). FIG. 17 illustrates the manner in which a cap 14 may be connected to the positioner 20 after the installation of the bioreactor lid 24, with the positioner extending through a port 22 therein to engage with the cap 14, and thus facilitate removal of the sample portion 16. FIG. 18 shows an arrangement wherein foldable wings 20c at the end of the connector may be folded into position over the sample portion 16 to temporarily hold it in place. Still further, the sample portion 16 may be held in position on the positioner 20 by positioning it in a bore 52 at the distal end of positioner 20, the bore including a flexible clamp 54, which is forced to a clamped position by an actuator 56, as shown in FIG. 19. FIG. 20 shows a similar arrangement in which an outer part 58 is used to cause an inner part 60 (either of which may connect to positioner, not shown) to clamp down onto the sample portion 16 and thus retain it in position (and which arrangement can be reversed by flexing the inner part to release the connection). FIG. 21 illustrates that a fastener 62 associated with the positioner 20 may be used to urge a holder 64 into a clamped position.

A method of assembling a bioreactor is also described. Using the FIG. 1 example simply for purposes of illustration, the bioreactor 12 may be assembled by positioning the material of the fixed bed 18 (structured or non-structured) in an interior compartment thereof. In the case of a structured bed, such as in FIG. 1A, the sample portion 16 may be positioned in the bed, and attached to the positioner 20 before or thereafter. The lid 24 may be applied to the bioreactor 12 such that the positioner passes into or through port, and the cap 14 put in place (including by connecting it to the positioner 20, if desired).

In the non-structured version, the material forming the fixed bed 18 may be positioned in the bioreactor 12, as above, and the same steps could be used. However, since the sample portion 16 need not be pre-positioned in a non-structured bed, the lid 24 may be applied, and the positioner 20 used to place the sample portion 16 in the bed 18. This may be done independent of the cap 14, or together with it, if the positioner 20 is connected to the cap.

Referring now to FIG. 22, a further embodiment of a sampler 300 for a bioreactor 312 is illustrated. In this embodiment, the sample portion 316 is positioned in the fixed bed 318, as per the other embodiments, and attached at a proximal end to a positioner 320 in the form of a flexible wire (which may be metal, plastic, or the like). A sleeve 328 may be sealed to a port 322 of the bioreactor 312 at one end, which guides the positioner 320 to connect with a sealed cap 340 for sealing with the proximal end of the sleeve 328. A coupling 350 may be formed by male and female parts 352, 354 for securing the cap 340 to the sleeve 328, and thus forming a seal that maintains the sterile condition of the bioreactor 312.

In order to sample the fixed bed 318, the sample portion 316 may be withdrawn by disconnecting the cap 340, which may or may not be connected to the positioner 320. If connected, the cap 340 may be pulled to withdraw the sample portion 316 from the fixed bed 318, through the internal passage of sleeve 328, and eventually out the proximal end thereof for access by the operator (or one or both the ends of the sleeve 328 may be sealed with the sample portion 316 therein). If not connected, then the cap 340 may be removed, and the positioner 320 manually withdrawn from the sleeve 328 to withdraw the sample portion 316. In the event of the wholesale withdrawal of the sample portion 316, the cap 340 may then be replaced to maintain the sterile condition, or the cap 340 may be placed on the port 322 if the sleeve 328 is removed.

The overhead space may in some circumstances be limited (such as when the bioreactor 312 is placed in a laminar flow cabinet), and so the sleeve 328 may be flexible and thus able to assume a depending position, as shown. This allows the operator to pull the positioner 320 for recovering the sample portion 316, without the need to access a space above the bioreactor 312. Instead of a fully flexible sleeve, it can be appreciated from FIG. 23 that the sleeve may include one or more ends, such as flexible ends 328a, 328b, which may be connected to one or more rigid portions, such as intermediate portion 328c or "elbow."

Turning now to FIG. 24, it is possible to use an actuator 360 for pulling the positioner 320 through the sleeve 328 to recover the sample portion 316. The actuator 360 may comprise a handle 362 connected to a rotor 364, to which a proximal end of the positioner 320 is connected (such as by winding the wire forming it in this embodiment). A stator 366 may receive the rotor 364, and include a seal 368 for permitting relative rotation while maintaining the sterile condition. A connector, such as a hose barb 370, may also be provided on the stator 366 for coupling with the sleeve 328.

Withdrawal of the sample portion 316 from the bed 318 is achieved by using the handle 362 to rotate the rotor 364, which may be manually done or automated. The flexible wire serving as positioner 320 is thus wrapped around the rotor 364, and the sample portion 316 withdrawn into the sleeve 328 (which, as noted above, may be sealed off distal of the location of the sample portion 316 therein to preserve sterility). As can be appreciated, this arrangement allows for the sterile condition to be maintained while the sample portion 316 is recovered.

An alternate version is shown in FIG. 25. The components are essentially the same, as indicated, but the "stator" 366 is connected (such as by welding) to a flexible bag 372, which surrounds the rotor 364 and maintains a sterile condition. The stator 366 may take the form of a cradle for rotatably supporting the rotor 364. Recovering the sample portion 316 may be accomplished by using handle 362 to rotate the rotor 364 through the flexible bag 372, which as in the earlier-described embodiment pulls the positioner 320 (by winding the wire on rotor 364).

A further embodiment of a sampler 400 for sampling a fixed bed 418 in a bioreactor 412 is shown with reference to FIG. 26. In this embodiment, the sample portion 416 is connected to a positioner 420 (which could be any positioner shown herein). The positioner 420 is releasably connected to a cap 414 associated with a port 422 of the bioreactor 412 (such as by engaging trunnions 422a that form a bayonet-style fitting; see, e.g., FIGS. 4, 5, and 6). The releasable connection may be established by a magnetic coupling created by corresponding magnet 414a in the cap 414 and a magnetic material 420a (including possible a ferromagnetic material) on the adjacent surface of the positioner 420. In one embodiment, the magnetic coupling is formed once the positioner 420 is in place in the bioreactor 412 and the cap 414 already in place, with the magnet 414a then introduced to the cap so as to avoid disrupting the positioner 420.

To allow for rotation of the cap 414 relative to the port 422, without interfering with (i.e., inducting rotation in) the positioner 420 and the attached sample portion 416, the positioner 420 and the port 422 may have matching surfaces. Specifically, the positioner 420 may include an outer projection 420b for aligning with a matching inner receiver 422b within the port 422, at a height corresponding to the formation of the magnetic coupling. The projection 420b and receiver 422b may be square in cross-section, and thus create an anti-rotation feature (but of course other shapes could also be used to achieve the same result). Hence, the cap 414 may be rotated for removal without rotating the positioner 420, which is retained by the engagement between the receiver 422b and projection 420b. Once the cap 414 is released, it may be removed from the port 422 to withdraw the positioner 420 and thus the sample portion 416 from the bioreactor 412.

Referring now to FIGS. 27 and 28, one particular example of a bioreactor 512 including one or more samplers 500 is shown (in the instant case, two are shown, but as noted above, any number may be provided). The bioreactor 512 includes one or more fixed beds, such as two vertically stacked fixed beds 518a, 518b in the illustrated example, which are arranged in an outer chamber 51a of the bioreactor 512 and may be the spiral beds shown in FIG. 1A and otherwise described herein. An inner chamber 512b is also provided for circulating fluid to or from the fixed bed(s), which fluid may be caused to flow by an associated agitator, such as an impeller 521 located in a lower compartment 512c of the bioreactor 512. The flow may be in a vertical direction within the fixed bed(s), such as from top to bottom or bottom to top. The fixed bed(s) could also be provided in the inner chamber 512b, with the outer chamber 512a serving to deliver fluid to and from the fixed bed(s) in the inner chamber.

In view of the substantially uniform conditions provided by a fixed bed in the form described herein, sampling any portion of the bed will typically provide a good indication of the cell growth conditions present at any portion therein. In any case, as shown in FIG. 27, it is possible to selectively position sample portions 516a, 516b at different locations (e.g., heights or depths in the vertical orientation shown) in the fixed bed(s), including in different stacked beds 518a, 518b, as shown, with positioner 520b and associated sample portion 516b simply being withdrawn through the bed(s) (such as along a pre-defined passage or tunnel) for recovery or inspection. The positioners 520 may be any of the embodiments described herein (including with sleeves, not shown), and the use before, during, and after bioprocessing may also be as described herein.

As can be appreciated, the disclosed sampler provides a unique opportunity to facilitate any of the steps herein by automation. For example, with reference to FIG. 29, this may be achieved as noted above by providing a system including a bioreactor 600 and an actuator 602, such as a motor or robotic device, to move (raise or lower) the positioner 20 to withdraw the sample portion 16 from the fixed bed 18 for analysis. A controller 604, such as a programmable logic controller, computer, or the like, may also be used to control the actuator 602 to activate, which could be done based on any number of parameters, such as time since the commencement of a cell culturing operation. The controller 604 may also receive outputs from one or more sensors 606 associated with the bioreactor 600 for sensing one or more parameters, such as pH, cell density, or the like, which are indicative of the state of the cell culturing operation. When one or more of the parameters reaches a pre-determined level, the controller 604 may actuate the associated actuator 602 to cause the positioner to withdraw the sample portion.

EXAMPLE

Figure 30:
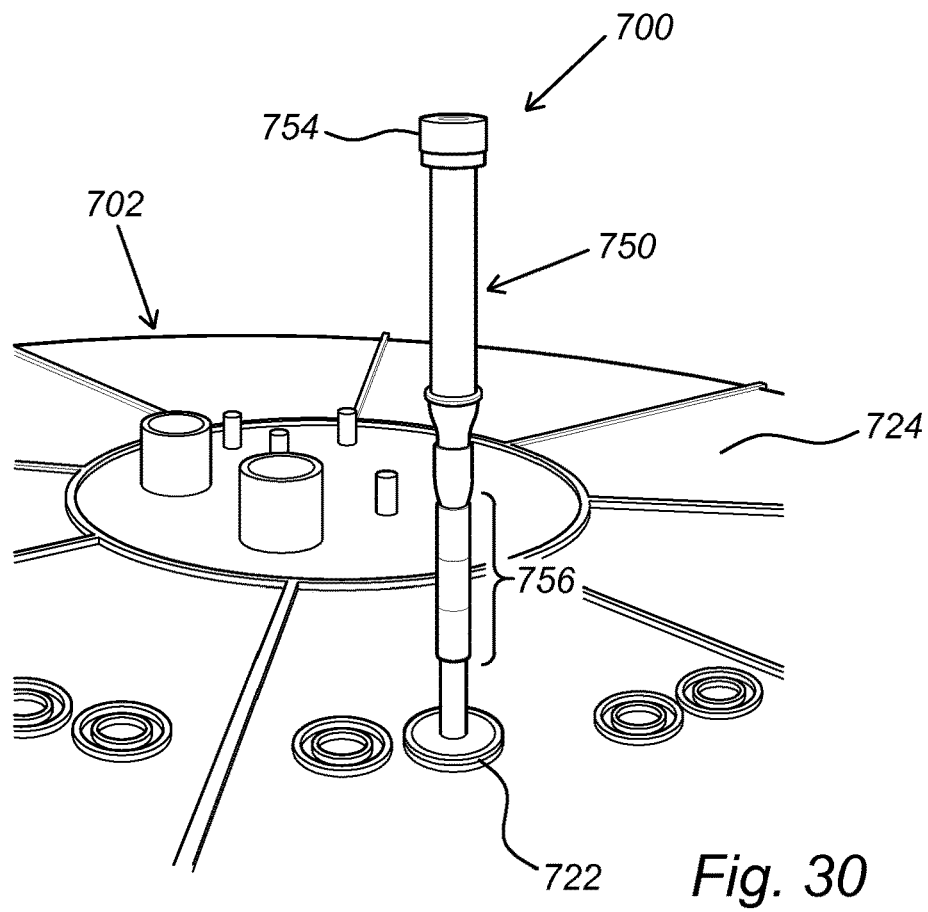
Figure 31:
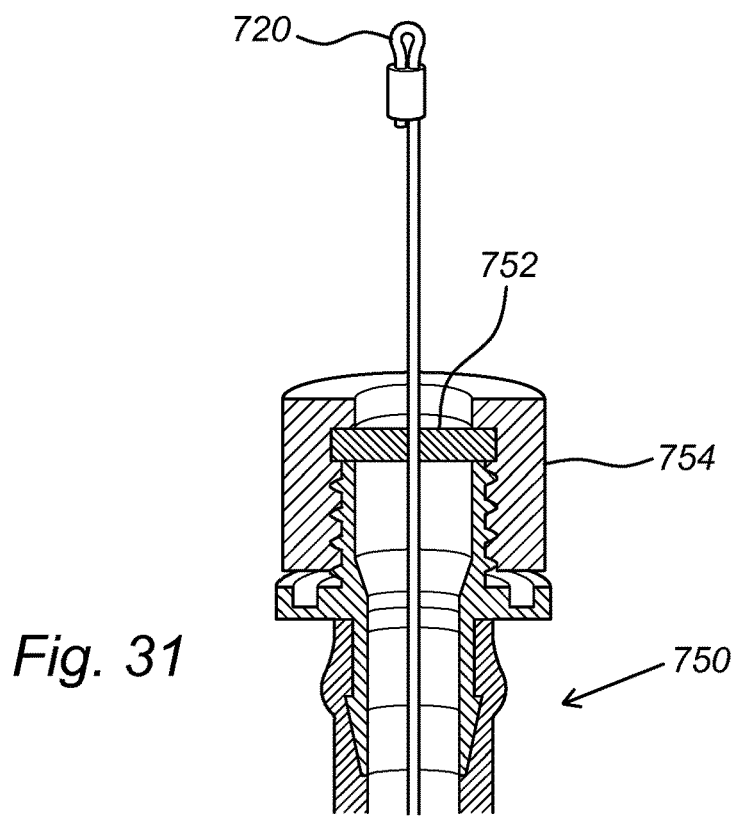
Figure 32:
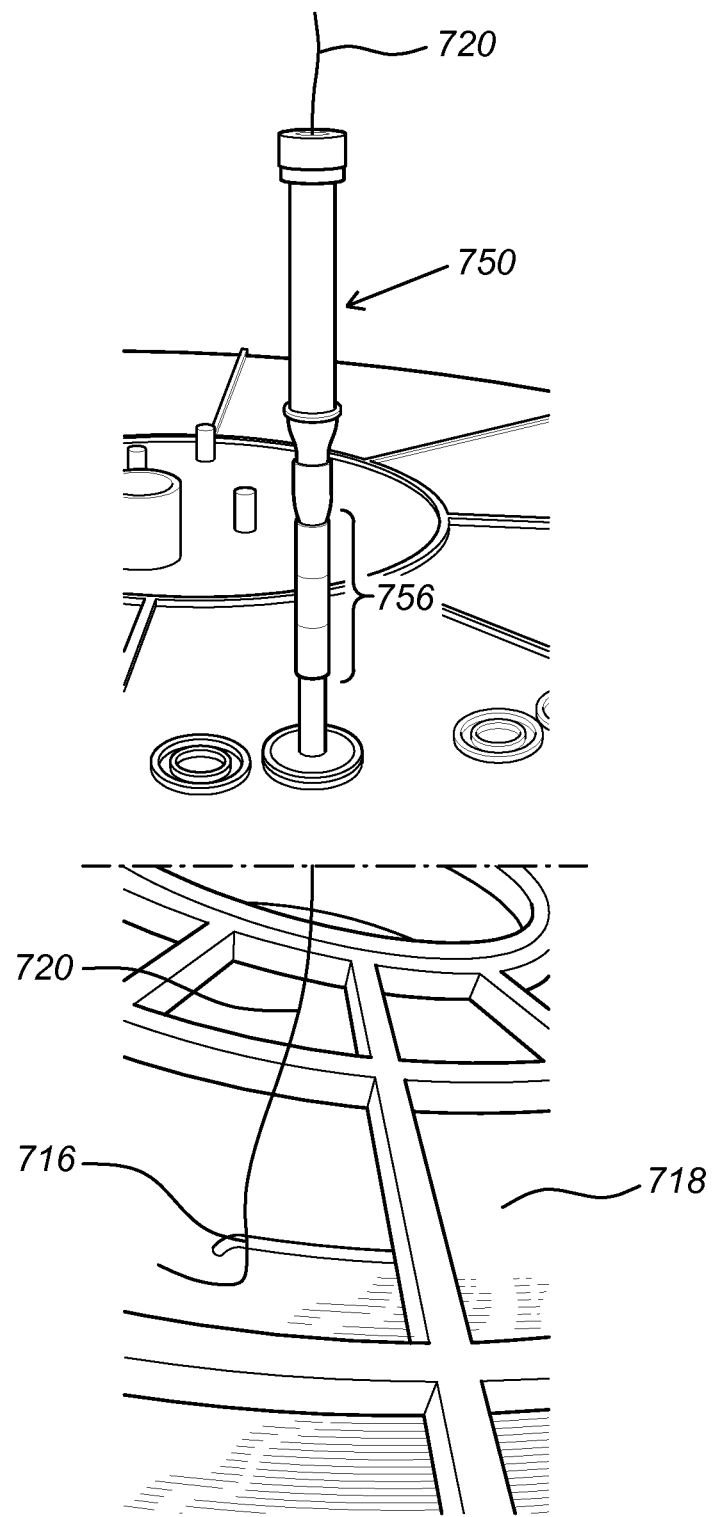

Turning now to FIGS. 30-37, an exemplary use of the sampler 700 is shown. In FIG. 30, it can be seen that the lid 724 of the bioreactor 702 includes a port 722, to which a partition or bather is provided in the form of a container or vial 750. With combined reference to FIGS. 31 and 32, it can be understood that the vial 750 includes a septum 752 through which the positioner in the form of a flexible wire 720 may pass for connecting to the sampler portion 716 located in the fixed bed 718 (such as between two cell immobilization layers thereof). The septum may 752 form part of a removable cap or cover 754, which may be crimped on (FIG. 30) or threaded onto (FIG. 31) the vial 750. An aseptic connection 756, such as a Quickseal device, is provided between the vial 750 and the port 722, and the wire 720 extends through it.

Figure 33:
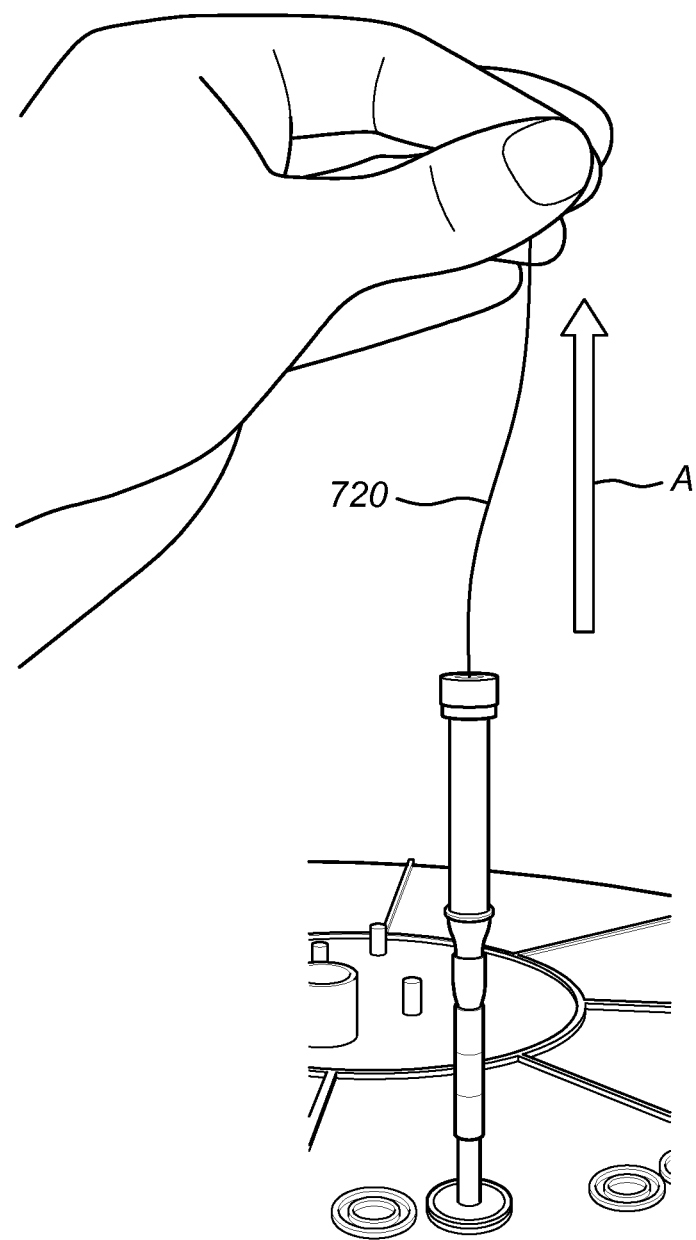

When it is desired to sample the cell culture associated with the bed 718, the positioner or wire 720 may be drawn through a continuous passage formed by the vial 750 and the connection 756, as indicated by action arrow A in FIG. 33. While a manual operation is shown, it could instead be automated, as indicated previously. Also, whether manual or automated, the decision to retrieve the sampler 716 could be based on the output of one or more sensors associated with the bioreactor 700.

Figure 34:
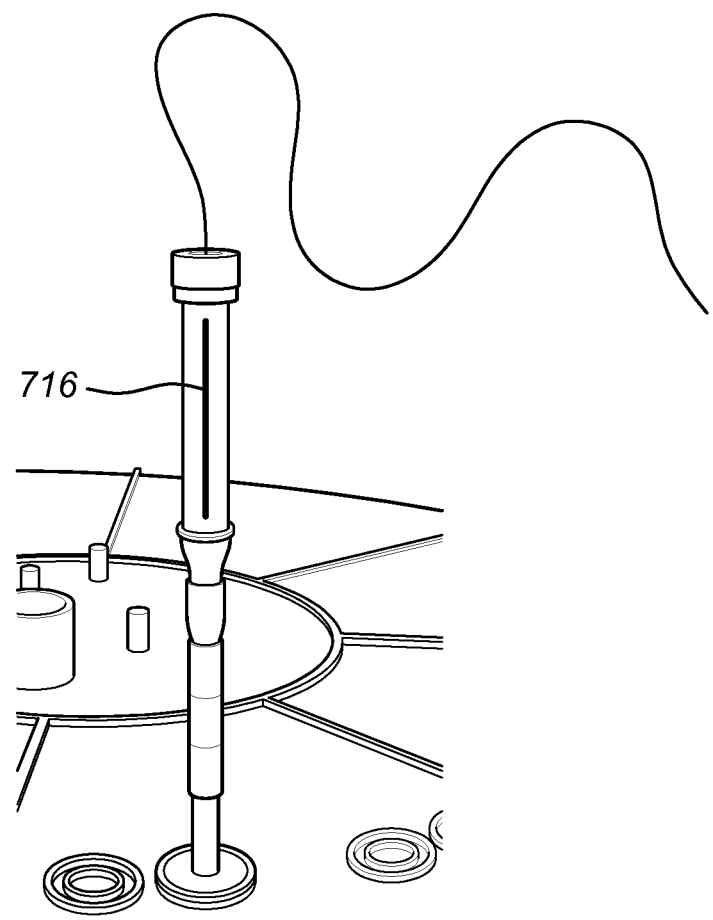
Figure 35:
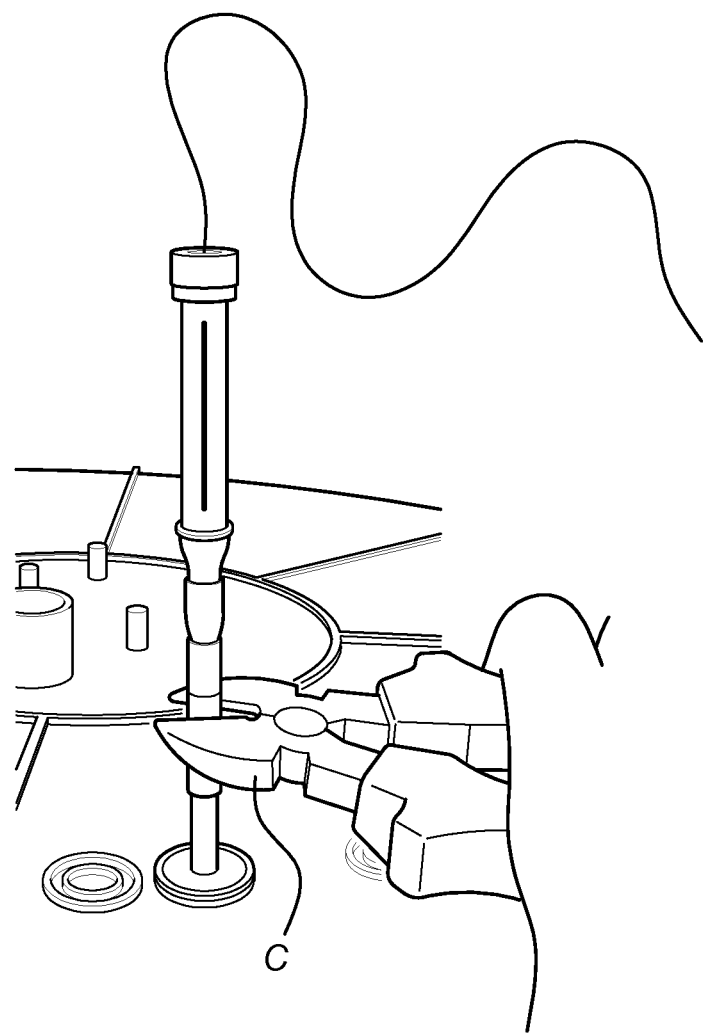
Figure 36:
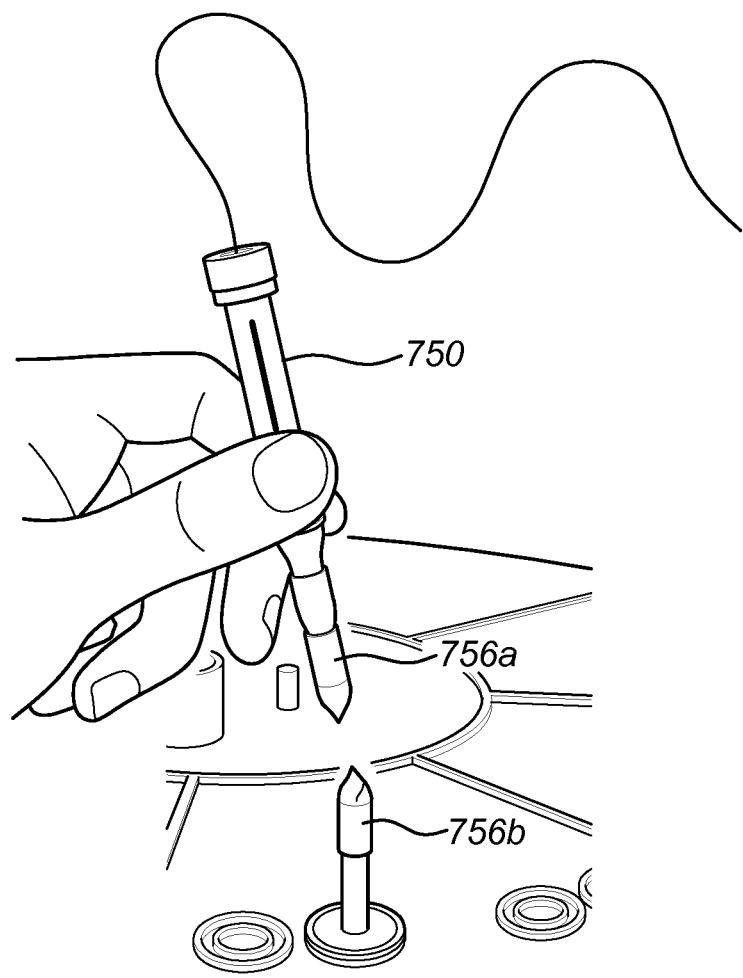
Figure 37:
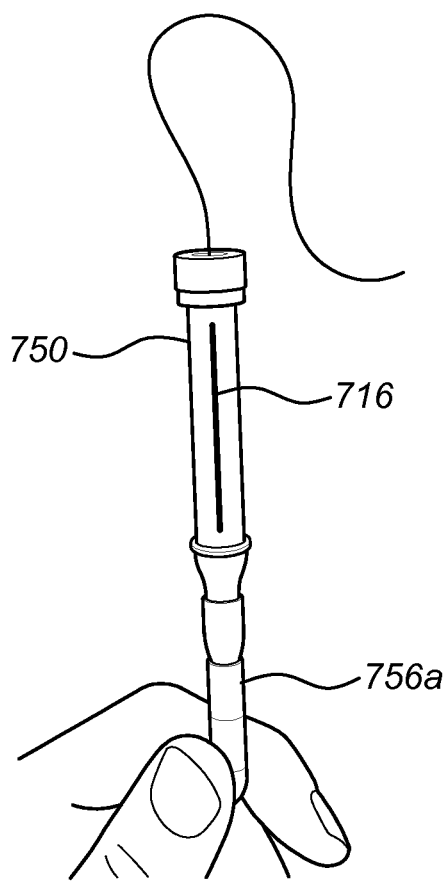
Figure 38:
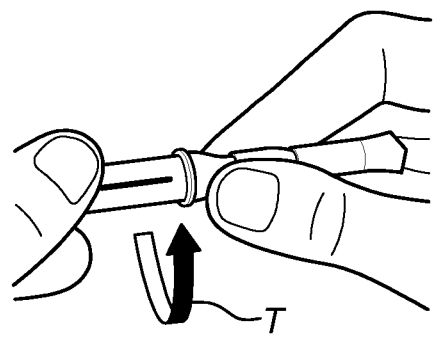
Figure 39:
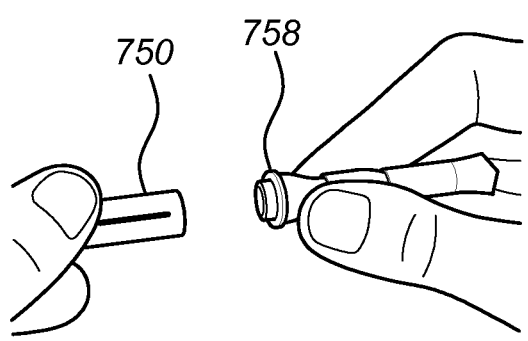
Figure 40:
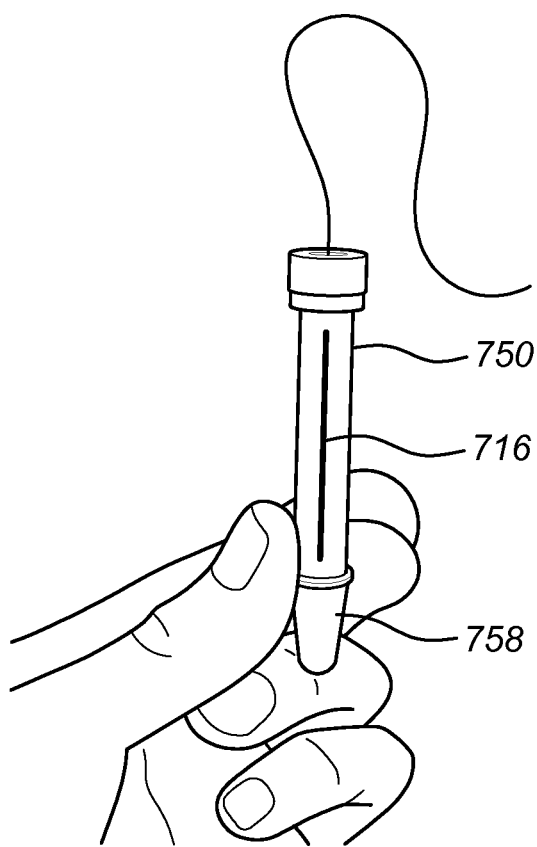

The wire 720 may be advanced until the sampler portion 716 is drawn into the vial 750, as shown in FIG. 34. Once fully located therein, the aseptic connection 756 may be disconnected, which in the case of the Quickseal device involves the use of a cutter C to crimp and sever the connection, thus separating the vial 750, as indicated in FIG. 36 (note connection portions 756a, 756b), while still maintaining sterile conditions. The remaining portion 756a of the now-separated connection 756 may then be removed (FIGS. 37 and 38), such as by twisting (arrow T) and the vial 750 sealed using a cap 758, as indicated in FIGS. 39 and 40, possibly after insertion of a reagent or the like. The vial 750 may then be used to study the growth of cells on the sampler portion 716, and thus give an accurate indication of the condition of the cell culture in the fixed bed 718 of the bioreactor 700. As examples, the study may involve counting the cells, coloration of the cells to evaluate some parameters (confluence, viability . . . ), or extraction of intra-cell viruses.

The vial 750 should of course have a volume that is greater than the volume of the sampler portion 716 it receives. It may in some cases be desirable to maintain a specific relationship between the volume of the vial 750 and the size of sampler portion 716 in terms of the surface area on which cells are grown. For example, the volume of the vial 750 may range from 0.5-1.0 milliliters, and the sampler portion 716 may have a surface area of about 1 to about 1.3 $cm^2$ and, more specifically, about 1.23 $cm^2$ for optimal results based on the number of cells present/unit volume of the vial.

Figure 41:
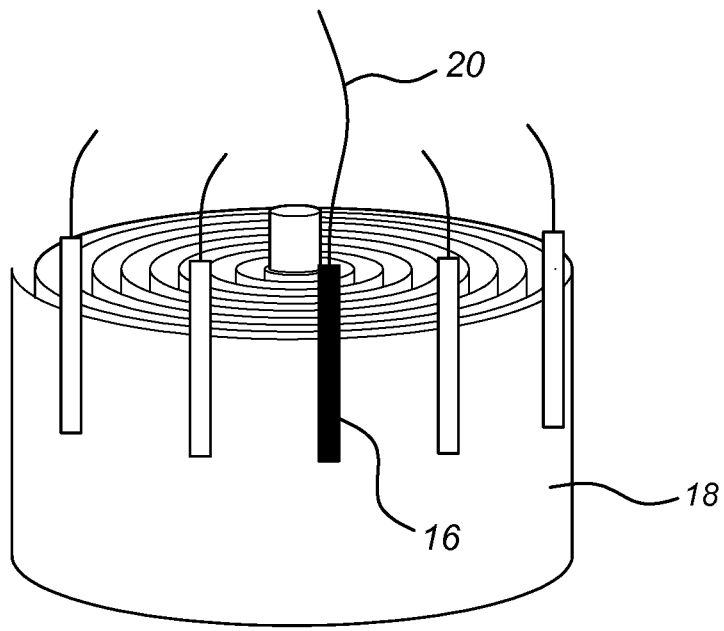
Figure 42:
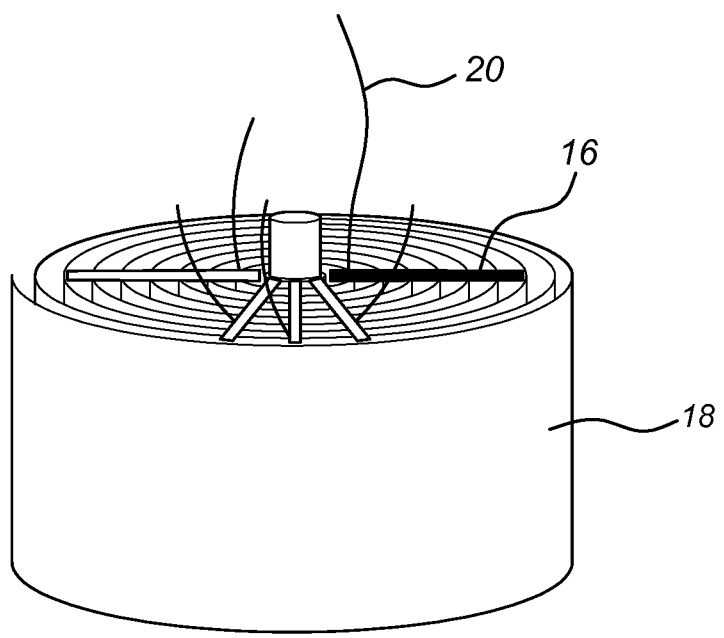
Figure 43:
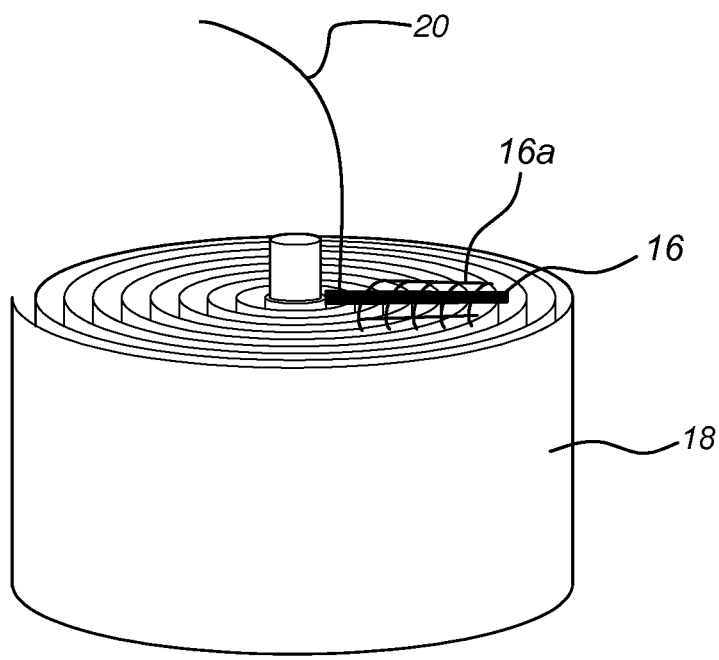
Figure 44:
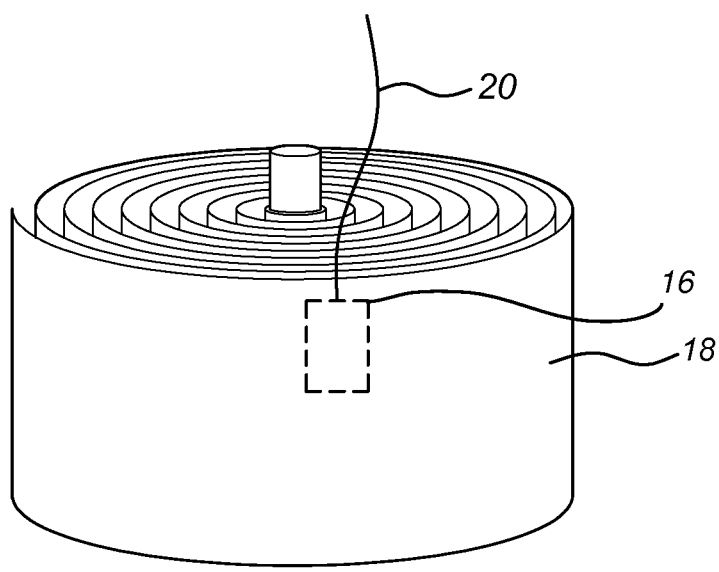

In any of the foregoing embodiments, the sample portion 16 may simply be in contact with the fixed bed 18 in a bioreactor (not shown), and need not be inserted or positioned within it. For example, as shown in FIGS. 41 and 42, the sample portion 16 may be positioned adjacent to and in contact with a surface of the fixed bed 18, such as a side surface (FIG. 41) or an upper surface (FIG. 42) thereof, and connected to the positioner 20, which again may be a flexible wire. As illustrated, a plurality of sample portions 16 may be provided, and may be on the surface(s) of the fixed bed 18, between layers of it, or both. The attachment may be achieved by a connector, such as a frangible one (adhesive). FIG. 43 further illustrates that a retainer 16a may be provided for retaining the sample portion 16 in place adjacent to the fixed bed 18. FIG. 44 illustrates the above-mentioned situation where the sample portion 16 forms part of the fixed bed 18 and is pre-cut or provided with perforations for ease of detachment. The pre-cut sample portion may be located anywhere in the fixed bed and in the illustrated embodiment the pre-cut sample is located close to the top of the bed. The bed 18 could be provided with one or more receivers, markers, indentations, notches, openings, voids, receiving portions, indicators, markings, guides or the like to indicate placement of a separate sample portion 16. When sampling of the cell culture is desired (which again may be done from any location in the bed 18 depending on the location(s) of the sample portion(s) 16), the positioner 20 is actuated (manually or automatically) to withdraw the sample portion from the bioreactor.

Finally, FIG. 45 shows a bioreactor 12 with a fixed bed 18 including a sample portion 16 connected to a positioner 20, which may be accessible via a cap 14 covering a port on the bioreactor lid 24. This figure illustrates in particular one exemplary flow patter through the bioreactor, which may be caused by an internal agitator, such as an impeller I. The flow arrangement may be such that fluid passes downwardly (arrow D) through an inner chamber, and then in a forward run (arrow F) to pass upwardly (arrow U) through the fixed bed 18 located outboard of the inner chamber. Flow is then returned (arrow R) via an internal column, where it may be exposed to a gas (air). As can be appreciated, with the same structural arrangement, the flow could be reversed.

This disclosure may be considered to relate to any or all of the following items, arranged in any combination, without limitation:

1. An apparatus for use with a cell culture system, comprising:
   a structured fixed bed including a removable sample portion for recovering a sample of cells from the cell culture system.
2. The apparatus of item 1, wherein the structured fixed bed comprises at least two layers of material adjacent to each other, the removable sample portion being located at least partially between the at least two layers.
3. The apparatus of item 2, wherein the at least two layers comprise: (1) cell immobilization layers, and the removable sample portion has a first side in contact with a first cell immobilization layer and a second side in contact with a second cell immobilization layer; or (2) one cell immobilization layer and one spacer layer.
4. The apparatus of any of items 1-3, wherein the removable sample portion comprises one or more fibers.
5. The apparatus of any of items 1-4, wherein the structured fixed bed and the removable sample portion comprise a non-woven material.
6. The apparatus of any of items 1-5, wherein the removable sample portion comprises a sheet of material.
7. The apparatus of any of items 1-6, wherein the structured fixed bed comprises a cell immobilization layer, and the sheet of material forming the removable sample portion is in direct contact with the cell immobilization layer.
8. The apparatus of any of items 1-7, further including a positioner mechanically connected to the removable sample portion by a connector.
9. The apparatus of any of items 1-8, wherein the structured fixed bed comprises a plurality of removable sample portions.
10. The apparatus of any of items 1-9, wherein the structured fixed bed comprises a roller or spiral bed.
11. The apparatus of any of items 1-10, wherein the removable sample portion is adjacent to the structured fixed bed.
12. The apparatus of any of items 1-11, wherein the removable sample portion is a perforated or pre-cut portion of the structured fixed bed.
13. A bioreactor including the apparatus of any of items 1-12.
14. The bioreactor of item 13, comprising an outer chamber for receiving the structured fixed bed with an upward flow of fluid, and an inner chamber for returning fluid flow to a lower portion of the bioreactor including an agitator.
15. An apparatus for use with a bioreactor for growing a cell culture, comprising:
    a fixed bed including a removable sample portion comprising one or more fibers for recovering a sample of cells from the cell culture.
16. The apparatus of item 15, wherein the fixed bed comprises an unstructured fixed bed.
17. The apparatus of item 15, wherein the fixed bed comprises a structured fixed bed.

18. The apparatus of any of items 15-17, wherein the removable sample portion comprises a non-woven material.
19. The apparatus of any of items 15-18, wherein the removable sample portion is between two layers of the fixed bed.
20. The apparatus of any of items 15-19, wherein the removable sample portion is adjacent to the fixed bed.
21. The apparatus of any of items 15-20, wherein the removable sample portion is a perforated or pre-cut portion of the structured fixed bed.
22. An apparatus for sampling a cell culture, comprising:
a bioreactor comprising a structured fixed bed including a removable sample portion; and
a sampler associated with the bioreactor for recovering the removable sample portion from the structured fixed bed.
23. The apparatus according to item 22 wherein the removable sample portion includes a positioner adapted for positioning the sample portion within the structured fixed bed, the positioner being accessible via a port in the bioreactor.
24. The apparatus of item 23, further including a support associated with the port by way of a releasable connection, such as a bayonet fitting including a slot on the support and a post on the port, a threaded connection, or a releasable latch, the support being connected to the positioner.
25. The apparatus according to item 24, wherein the support is fixed to the positioner, or releasably connected to the positioner, such as by a flexible portion for releasably engaging a portion of the positioner for movement together in an axial direction, but allowing for the support to rotate without imparting rotation to the positioner.
26. The apparatus of item 24, wherein the support comprises a frangible connection for separating the support into multiple portions for removal of the removable sample portion.
27. The apparatus of any of items 22-26, wherein the sampler comprises a cutter for forming the removable sample portion of the structured fixed bed.
28. The apparatus of any of items 22-37, wherein the sampler comprises a groove for engaging a locking pin associated with the port for guiding the sampler into position.
29. The apparatus of any of items 22-28, further including a container for maintaining a sterile condition of the removable sample portion when removed from the bioreactor.
30. The apparatus of item 29, wherein the container connects to the bioreactor via an aseptic connection so as to maintain a sterile condition within a compartment defined by the container and including the sampler, and also a sterile condition of the bioreactor.
31. The apparatus of item 29 or item 30, wherein the container comprises a septum for receiving a connector connected to the removable sample portion.
32. The apparatus of any of items 29-31, wherein the container comprises a flexible sleeve.
33. The apparatus of item 32, wherein the flexible sleeve is connected to a rigid elbow.
34. The apparatus according to any of items 22-33, wherein the removable sample portion includes a positioner connected to the removable sample portion, the positioner being associated with an actuator for withdrawing the removable sample portion from the structured fixed bed.
35. The apparatus according to item 34, wherein the actuator comprises a stator and a rotor.
36. The apparatus according to item 34 or item 35, wherein the actuator is connected to a sleeve for receiving a positioner connected to the sample portion.
37. The apparatus of item 35 or item 36, wherein the stator comprises a flexible bag surrounding the rotor.
38. The apparatus of item 35, item 36, or item 37, wherein the stator comprises a cradle for cradling the rotor.
39. The apparatus of any of items 34-38, further including a controller for controlling the actuator.
40. The apparatus of item 39, wherein the controller is adapted for receiving an output signal from at least one sensor associated with the bioreactor.
41. The apparatus of any of items 22-40, wherein the removable sample portion is connected to a positioner forming a releasable connection with a cap for a port of the bioreactor.
42. The apparatus of item 41, wherein the releasable connection comprises a magnetic coupling.
43. The apparatus of item 41, wherein the port includes a receiver for receiving a projection of the positioner in a manner that prevents relative rotation.
44. The apparatus of any of items 22-43, wherein the structured fixed bed comprises a spiral bed.
45. The apparatus of any of items 22-43, wherein the removable sample portion is adjacent to the structured fixed bed.
46. The apparatus of any of items 22-43, wherein the removable sample portion is a perforated or pre-cut portion of the structured fixed bed.
47. An apparatus for sampling a cell culture, comprising:
a bioreactor comprising a bed including a removable sample portion; and
a sampler associated with the bioreactor for recovering the removable sample portion from the bed, the sampler comprising a positioner releasably connected to the removable sample portion.
48. The apparatus of item 47, wherein the positioner is releasably connected to the removable sample portion by a clamp.
49. The apparatus of any of items 47-48, wherein the removable sample portion is within or adjacent to the structured fixed bed.
50. The apparatus any of items 47-48, wherein the removable sample portion is a perforated or pre-cut portion of the structured fixed bed.
51. An apparatus for sampling a cell culture associated with a bed in a bioreactor having a port, comprising:
a sampler associated with the bioreactor for recovering a sample portion of the bed via the port, the sampler including an actuator for withdrawing the sample portion from the bed.
52. The apparatus according to item 51, wherein the actuator is connected to a container for receiving a positioner connected to the sample portion.
53. The apparatus according to item 51 or item 52, wherein the actuator comprises a stator and a rotor.
54. The apparatus of item 53, wherein the stator comprises a flexible bag surrounding the rotor.
55. The apparatus of item 53 or item 54, wherein the stator comprises a cradle for cradling the rotor.
56. The apparatus of any of items 51-55, further including a controller for controlling the actuator.
57. The apparatus of item 56, wherein the controller is adapted for receiving an output signal from at least one sensor associated with the bioreactor.
58. The apparatus of any of items 51-57, wherein the bed comprises a structured fixed bed including at least two layers, and the sample portion comprises a sheet of material located between at least two layers.

59. The apparatus of any of items 51-57, wherein the removable sample portion is within or adjacent to the structured fixed bed.

60. The apparatus of any of items 51-57, wherein the removable sample portion is a perforated or pre-cut portion of the structured fixed bed.

61. A method of sampling a cell culture in a bioreactor having a structured fixed bed, comprising:
recovering a removable sample portion from the structured fixed bed of the bioreactor.

62. The method of item 61, wherein the structured fixed bed comprises at least two layers, and the method comprises positioning the removable sample portion at least partially between the at least two layers prior to the recovering step.

63. The method of item 61 or item 62, wherein the recovering step comprises withdrawing a positioner connected to the removable sample portion from the bioreactor until the removable sample portion is received in a container connected to the bioreactor by an aseptic connector.

64. The method of item 63, wherein the withdrawing step comprises using an actuator controlled by a controller based on a sensed condition of the bioreactor.

65. The method of any of items 61-64, further including the step of counting the cells removed on the removable sample portion.

66. The method of any of items 61-64, further including the step of coloration of the cells.

67. The method of any of items 61-66, further including the step of extracting intra-cell viruses from the cells removed on the removable sample portion.

68. A method for inserting a sample portion in a fixed bed having two or more layers, comprising:
positioning the sample portion within or adjacent to the two or more layers of the fixed bed.

69. A method for manufacturing a fixed bed wherein the fixed bed comprises one or more sample portions, the method comprising introducing means for detaching the sample portion from the rest of the fixed bed.

70. The method of item 69, further including the step of perforating or pre-cutting the bed to form the one or more sample portions.

71. The method of item 69, further including the step of growing cells on the one or more sample portions.

As used herein, the following terms have the following meanings:

"A", "an", and "the" as used herein refers to both singular and plural referents unless the context clearly dictates otherwise. By way of example, "a compartment" refers to one or more than one compartment.

"About," "substantially," or "approximately," as used herein referring to a measurable value, such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

While preferred embodiments of the present invention have been shown and described herein, it will be obvious to those skilled in the art that such embodiments are provided by way of example only. Numerous variations, changes, and substitutions will now occur to those skilled in the art without departing from the invention. For example, while the bioreactor is shown in a vertical orientation, it could be used in any orientation. It should be understood that various alternatives to the embodiments of the invention described herein may be employed in practicing the invention. It is intended that the following claims define the scope of the protection under the applicable law and that methods and structures within the scope of these claims and their equivalents be covered thereby.

What is claimed:

1. An apparatus for use with a cell culture system, comprising:
a structured fixed bed comprising a substrate material for achieving cell growth and cell immobilization, said structured fixed bed comprising a spiral configuration with at least two layers in direct contact with one another;
a removable sample portion comprising the substrate material, the removable sample portion being separate from the structured fixed bed;
wherein the removable sample portion is located at least partially between the at least two layers.

2. The apparatus of claim 1, wherein the at least two layers comprise:
(1) cell immobilization layers, and the removable sample portion has a first side in contact with a first cell immobilization layer and a second side in contact with a second cell immobilization layer;
or (2) one cell immobilization layer and one spacer layer.

3. The apparatus of claim 1, wherein the removable sample portion comprises one or more fibers.

4. The apparatus of claim 1, wherein the structured fixed bed and the removable sample portion comprise a non-woven material.

5. The apparatus of claim 1, wherein the removable sample portion comprises a sheet of the substrate material.

6. The apparatus of claim 5, wherein the structured fixed bed comprises a cell immobilization layer, and the sheet of material forming the removable sample portion is in direct contact with the cell immobilization layer.

7. The apparatus of claim 1, further including a positioner mechanically connected to the removable sample portion by a connector.

8. The apparatus of claim 1, further including a plurality of removable sample portions.

9. The apparatus of claim 1, further including a bioreactor for housing the structured fixed bed and a sampler associated with the bioreactor for recovering the removable sample portion from the structured fixed bed.

10. The apparatus of claim 1, wherein the removable sample portion is prepositioned within the structured fixed bed at a specific location, and wherein the removable sample portion is adapted for removal from the specific location.

11. The apparatus of claim 1, wherein the removable sample portion comprises an elongated strip of the substrate material.

* * * * *